United States Patent
Emmons et al.

(10) Patent No.: US 11,837,363 B2
(45) Date of Patent: Dec. 5, 2023

(54) REMOTE MANAGEMENT OF PATIENT ENVIRONMENT

(71) Applicant: Hill-Rom Services, Inc., Batesville, IN (US)

(72) Inventors: Kirsten M. Emmons, Batesville, IN (US); Richard H. Heimbrock, Batesville, IN (US); Phillip Kuhn, Rushville, IN (US); David L. Ribble, Indianapolis, IN (US); Sandra Shuster, Chicago, IL (US); Dan R. Tallent, Hope, IN (US); Pauline Wong, Buffalo Grove, IL (US); Lori Ann Zapfe, Milroy, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 170 days.

(21) Appl. No.: 17/453,227

(22) Filed: Nov. 2, 2021

(65) Prior Publication Data

US 2022/0139549 A1 May 5, 2022

Related U.S. Application Data

(60) Provisional application No. 63/109,585, filed on Nov. 4, 2020.

(51) Int. Cl.
*G16H 40/67* (2018.01)
*G16H 80/00* (2018.01)
*G16H 10/60* (2018.01)

(52) U.S. Cl.
CPC ............. *G16H 40/67* (2018.01); *G16H 10/60* (2018.01); *G16H 80/00* (2018.01)

(58) Field of Classification Search
CPC ......... G16H 40/67; G16H 10/60; G16H 80/00
See application file for complete search history.

(56) References Cited

U.S. PATENT DOCUMENTS

| | | | |
|---|---|---|---|
| 5,544,649 A | 8/1996 | David et al. | |
| 5,771,511 A | 6/1998 | Kummer et al. | |
| 6,241,668 B1 | 6/2001 | Herzog | |
| 6,789,105 B2 | 9/2004 | Ludwig et al. | |
| 6,804,656 B1 | 10/2004 | Rosenfeld et al. | |
| 6,914,622 B1 | 7/2005 | Smith et al. | |
| 6,925,357 B2 | 8/2005 | Wang et al. | |
| 7,011,629 B2 | 3/2006 | Bulat | |
| 7,017,208 B2 | 3/2006 | Weismiller et al. | |
| 7,133,062 B2 | 11/2006 | Castles et al. | |
| 7,142,945 B2 | 11/2006 | Wang et al. | |
| 7,164,969 B2 | 1/2007 | Wang et al. | |
| 7,164,970 B2 | 1/2007 | Wang et al. | |
| 7,185,282 B1* | 2/2007 | Naidoo | H04N 21/4131 348/E7.071 |

(Continued)

*Primary Examiner* — Nabil H Syed
*Assistant Examiner* — Cal J Eustaquio
(74) *Attorney, Agent, or Firm* — Merchant & Gould P.C.

(57) ABSTRACT

A computing device for remotely engaging and managing a patient environment displays a video feed of a patient environment, and provides user inputs that, when selected, allow a caregiver to remotely change a condition in the patient environment. Access to the user inputs is restricted based on at least one of a distance between the computing device and the patient environment, credentials of the caregiver, and a condition of a patient in the patient environment.

20 Claims, 12 Drawing Sheets

(56) References Cited

U.S. PATENT DOCUMENTS

| | | |
|---|---|---|
| 7,256,708 B2 | 8/2007 | Rosenfeld et al. |
| 7,283,153 B2 | 10/2007 | Provost et al. |
| 7,289,883 B2 | 10/2007 | Wang et al. |
| 7,310,570 B2 | 12/2007 | Wang et al. |
| 7,477,285 B1 | 1/2009 | Johnson |
| 7,590,550 B2 | 9/2009 | Schoenberg |
| 7,612,666 B2 | 11/2009 | Badawy |
| 7,612,999 B2 | 11/2009 | Clark et al. |
| 7,691,059 B2 | 4/2010 | Bulat |
| 7,761,185 B2 | 7/2010 | Wang et al. |
| 7,769,605 B2 | 8/2010 | Brown |
| 7,791,866 B2 | 9/2010 | Clark et al. |
| 7,835,926 B1 | 11/2010 | Naidoo et al. |
| 7,835,928 B2 | 11/2010 | Schoenberg |
| 7,844,657 B2 | 11/2010 | Novak |
| 7,911,348 B2 | 3/2011 | Rogers |
| 7,912,733 B2 | 3/2011 | Clements et al. |
| 7,945,457 B2 | 5/2011 | Zaleski |
| 7,970,633 B2 | 6/2011 | Bulat |
| 7,987,069 B2 | 7/2011 | Rodgers et al. |
| 7,990,691 B2 | 8/2011 | Clark et al. |
| 8,069,420 B2 | 11/2011 | Plummer |
| 8,179,418 B2 | 5/2012 | Wright et al. |
| 8,273,018 B1 | 9/2012 | Fackler et al. |
| 8,321,284 B2 | 11/2012 | Clements et al. |
| 8,451,314 B1 | 5/2013 | Cline et al. |
| 8,471,899 B2 | 6/2013 | Johnson |
| 8,510,130 B2 | 8/2013 | Scoenberg |
| 8,526,176 B2 | 9/2013 | Clark et al. |
| 8,554,195 B2 | 10/2013 | Rao |
| 8,600,773 B2 | 12/2013 | Schoenberg |
| 8,618,918 B2 | 12/2013 | Tallent et al. |
| 8,635,084 B2 | 1/2014 | Phillips |
| 8,670,017 B2 | 3/2014 | Stuart et al. |
| 8,675,059 B2 | 3/2014 | Johnson et al. |
| 8,676,603 B2 | 3/2014 | Johnson |
| 8,688,471 B2 | 4/2014 | Chien |
| 8,719,047 B2 | 5/2014 | Schoenberg |
| 8,731,512 B2 | 5/2014 | Borras et al. |
| 8,780,165 B2 | 7/2014 | Wang et al. |
| 8,799,010 B2 | 8/2014 | Kandinya et al. |
| 8,849,679 B2 | 9/2014 | Wang et al. |
| 8,849,680 B2 | 9/2014 | Wright et al. |
| 8,878,888 B2 | 11/2014 | Rosenfeld |
| 8,986,204 B2 | 3/2015 | Pacey et al. |
| 8,996,392 B2 | 3/2015 | Cashman et al. |
| 9,030,292 B2 | 5/2015 | Torgersrud et al. |
| 9,041,810 B2 | 5/2015 | Ecker et al. |
| 9,043,217 B2 | 5/2015 | Cashman et al. |
| 9,089,972 B2 | 7/2015 | Stuart et al. |
| 9,098,611 B2 | 8/2015 | Pinter et al. |
| 9,160,783 B2 | 10/2015 | Pinter |
| 9,204,823 B2 | 12/2015 | Derenne et al. |
| RE45,870 E | 1/2016 | Wang et al. |
| 9,288,439 B2 | 3/2016 | Bloms et al. |
| 9,311,540 B2 | 4/2016 | Ecker et al. |
| 9,318,012 B2 | 4/2016 | Johnson et al. |
| 9,398,058 B2 | 7/2016 | Vuong |
| 9,403,805 B2 | 8/2016 | Bulat |
| 9,468,360 B2 | 10/2016 | Berci |
| 9,485,475 B2 | 11/2016 | Speier et al. |
| 9,491,277 B2 | 11/2016 | Vincent |
| 9,571,789 B2 | 2/2017 | Pinter et al. |
| 9,579,047 B2 | 2/2017 | Clark et al. |
| 9,602,765 B2 | 3/2017 | Wang et al. |
| 9,619,849 B2 | 4/2017 | Rock |
| 9,635,320 B2 | 4/2017 | Greco et al. |
| 9,641,799 B2 | 5/2017 | Smurro |
| 9,648,060 B2 | 5/2017 | Ahmed |
| 9,761,112 B2 | 9/2017 | Similowski et al. |
| 9,794,523 B2 | 10/2017 | Greco et al. |
| 9,830,423 B2 | 11/2017 | Biswas et al. |
| 9,838,645 B2 | 12/2017 | Hyde et al. |
| 9,866,797 B2 | 1/2018 | Clark et al. |
| 9,886,551 B2 | 2/2018 | Schoenberg |
| 9,888,976 B2 | 2/2018 | Costa da Cruz |
| 9,892,311 B2 | 2/2018 | Kusens et al. |
| 9,934,427 B2 | 4/2018 | Derenne et al. |
| 9,937,090 B2 | 4/2018 | Hayes et al. |
| 10,007,761 B2 | 6/2018 | Sadler et al. |
| 10,019,553 B2 | 7/2018 | Sanford |
| 10,028,646 B2 | 7/2018 | Gazdzinski |
| 10,034,038 B2 | 7/2018 | Rai et al. |
| 10,034,979 B2 | 7/2018 | Bechtel et al. |
| 10,037,821 B2 | 7/2018 | Johnson et al. |
| 10,044,989 B2 | 8/2018 | Greco et al. |
| 10,045,716 B2 | 8/2018 | Clark et al. |
| 10,055,961 B1 | 8/2018 | Johnson et al. |
| 10,057,337 B2 | 8/2018 | Kyser et al. |
| 10,059,000 B2 | 8/2018 | Herzog et al. |
| 10,068,302 B2 | 9/2018 | Gencarelli et al. |
| 10,074,148 B2 | 9/2018 | Cashman et al. |
| 10,078,951 B2 | 9/2018 | Kusens |
| 10,096,223 B1 | 10/2018 | Kusens |
| 10,130,311 B1 | 11/2018 | De Sapio et al. |
| 10,147,297 B2 | 12/2018 | Kusens |
| 10,210,378 B2 | 2/2019 | Kusens et al. |
| 10,210,395 B2 | 2/2019 | Kusens |
| 10,212,359 B2 | 2/2019 | Neff et al. |
| 10,216,906 B2 | 2/2019 | Desgranges et al. |
| 10,217,342 B2 | 2/2019 | Kusens |
| 10,223,681 B2 | 3/2019 | Cashman et al. |
| 10,225,522 B1 | 3/2019 | Kusens |
| 10,271,729 B2 | 4/2019 | Greiner et al. |
| 10,276,019 B2 | 4/2019 | Johnson et al. |
| 10,290,071 B2 | 5/2019 | Heil et al. |
| 10,296,722 B2 | 5/2019 | Rock |
| 10,315,312 B2 | 6/2019 | Wang et al. |
| 10,320,903 B2 | 6/2019 | Newman et al. |
| 10,331,856 B1 | 6/2019 | Schopke |
| 10,332,639 B2 | 6/2019 | Smurro |
| 10,348,777 B2 | 7/2019 | Knotts |
| 10,354,051 B2 | 7/2019 | Hickle et al. |
| 10,357,156 B2 | 7/2019 | Sommer et al. |
| 10,372,873 B2 | 8/2019 | Johnson |
| 10,382,727 B2 | 8/2019 | Clark et al. |
| 10,387,720 B2 | 8/2019 | Johnson et al. |
| 10,390,738 B2 | 8/2019 | Clark et al. |
| 10,395,328 B2 | 8/2019 | Phillips et al. |
| 10,397,521 B2 | 8/2019 | Vitale et al. |
| 10,417,383 B2 | 9/2019 | Krimsky et al. |
| 10,430,552 B2 | 10/2019 | Mihai |
| 10,447,745 B2 | 10/2019 | Vuong |
| 10,471,588 B2 | 11/2019 | Wright et al. |
| 10,483,007 B2 | 11/2019 | Celmins et al. |
| 10,489,554 B2 | 11/2019 | Hickle et al. |
| 10,540,876 B2 | 1/2020 | Johnson et al. |
| 10,565,352 B2 | 2/2020 | Eaton, Jr. et al. |
| 10,586,020 B2 | 3/2020 | Madhavan et al. |
| 10,600,516 B2 | 3/2020 | Merkin |
| 10,603,792 B2 | 3/2020 | Lai et al. |
| 10,617,299 B2 | 4/2020 | Sanchez et al. |
| 10,630,941 B2 | 4/2020 | Greco et al. |
| 10,643,446 B2 | 5/2020 | Kusens et al. |
| 10,645,346 B2 | 5/2020 | Clark et al. |
| 10,665,345 B2 | 5/2020 | Seriani |
| 10,682,763 B2 | 6/2020 | Pinter |
| 10,694,144 B2 | 6/2020 | Shaya |
| 10,709,359 B2 | 7/2020 | Clark et al. |
| 10,716,474 B2 | 7/2020 | Bodurka et al. |
| 10,726,952 B2 | 7/2020 | Sanford |
| 10,762,994 B2 | 9/2020 | Seriani |
| 10,768,668 B2 | 9/2020 | Herzog et al. |
| 10,790,059 B2 | 9/2020 | Woods |
| 10,842,378 B2 | 11/2020 | Verma |
| 10,848,713 B2 | 11/2020 | Vitale et al. |
| 10,873,855 B1 | 12/2020 | Yuresko et al. |
| 10,878,220 B2 | 12/2020 | Kusens |
| 10,882,180 B2 | 1/2021 | Wright et al. |
| 10,887,545 B2 | 1/2021 | Stuart et al. |
| 10,893,233 B1 | 1/2021 | Guo et al. |
| 10,916,347 B2 | 2/2021 | Seriani |
| 10,922,946 B2 | 2/2021 | Kusens et al. |
| 10,936,698 B2 | 3/2021 | Hodge |

(56) References Cited

U.S. PATENT DOCUMENTS

| | | | |
|---|---|---|---|
| 10,969,583 B2 | 4/2021 | Hresko et al. | |
| 10,973,471 B2 | 4/2021 | Rose et al. | |
| 10,978,202 B2 | 4/2021 | Hamilton et al. | |
| 10,984,916 B2 | 4/2021 | Celmins et al. | |
| 11,043,307 B2 | 6/2021 | Smurro | |
| 2002/0014951 A1* | 2/2002 | Kramer | G16H 10/60 340/286.07 |
| 2002/0044059 A1 | 4/2002 | Reeder et al. | |
| 2004/0019406 A1 | 1/2004 | Wang et al. | |
| 2004/0143421 A1 | 7/2004 | Wang et al. | |
| 2005/0021187 A1 | 1/2005 | Wang et al. | |
| 2005/0204438 A1 | 9/2005 | Wang et al. | |
| 2007/0073555 A1 | 3/2007 | Buist | |
| 2007/0112464 A1 | 5/2007 | Wang et al. | |
| 2007/0120689 A1 | 5/2007 | Zerhusen et al. | |
| 2007/0291128 A1 | 12/2007 | Wang et al. | |
| 2009/0112069 A1* | 4/2009 | Kanamori | A61B 5/113 600/300 |
| 2019/0228863 A1* | 7/2019 | Dharwad | G16H 20/17 |
| 2020/0020462 A1 | 1/2020 | Garrett et al. | |
| 2020/0204621 A1 | 6/2020 | Brown et al. | |
| 2020/0305766 A1 | 10/2020 | Durlach et al. | |
| 2020/0357511 A1 | 11/2020 | Sanford | |
| 2021/0120210 A1 | 4/2021 | Vitale et al. | |

\* cited by examiner

REMOTE MANAGEMENT OF PATIENT ENVIRONMENT

BACKGROUND

Caregivers are often assigned to multiple patients. The patients can be located in different rooms requiring caregivers to walk from room to room to provide direct patient care, which limits the amount of time that caregivers can spend with each patient. Also, caregivers often have to manage administrative tasks related to the care of their assigned patients, which can further reduce the amount of time that they can dedicate to direct patient care.

Additionally, infectious diseases can affect the ability of caregivers to provide direct patient care. For example, in order to prevent the spread of an infectious disease, caregivers must wear personal protective equipment (PPE). The time that is needed for caregivers to put on the PPE further limits the amount of time that they can spend with their assigned patients and also increases the costs and risks associated with providing direct patient care.

SUMMARY

In general terms, the present disclosure relates to remote engagement and management of a patient environment. Various aspects are described in this disclosure, which include, but are not limited to, the following aspects.

One aspect relates to a computing device for remotely managing a patient environment. The computing device comprises at least one processing device; and at least one computer readable data storage device storing software instructions that, when executed by the at least one processing device, cause the computing device to: display a video feed of the patient environment; and provide user inputs that, when selected, allow a caregiver to remotely change a condition in the patient environment, wherein access to the user inputs is restricted based on at least one of a distance between the computing device and the patient environment, credentials of the caregiver, and a current condition of a patient in the patient environment.

Another aspect relates to a computer-readable data storage medium comprising software instructions that, when executed, cause at least one computing device to: display a video feed of a patient environment; provide a user input that, when selected, allows a caregiver to communicate with a patient in the patient environment, the caregiver being remotely located away from the patient; and provide one or more user inputs that, when selected, allow the caregiver to remotely manage the patient environment, wherein access to the one or more additional user inputs is restricted based on at least one of a distance between the at least one computing device and the patient environment, credentials of the caregiver, and a condition of the patient.

Another aspect relates to a method of remotely managing a patient environment. The method comprises displaying a video feed of the patient environment; providing a user input allowing a caregiver to communicate with a patient in the patient environment, the caregiver being remotely located away from the patient; and providing one or more user inputs that, when selected, allow the caregiver to remotely manage the patient environment, wherein access to the one or more additional user inputs is restricted based on at least one of a distance between a computing device and the patient environment, credentials of the caregiver, and a condition of the patient.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
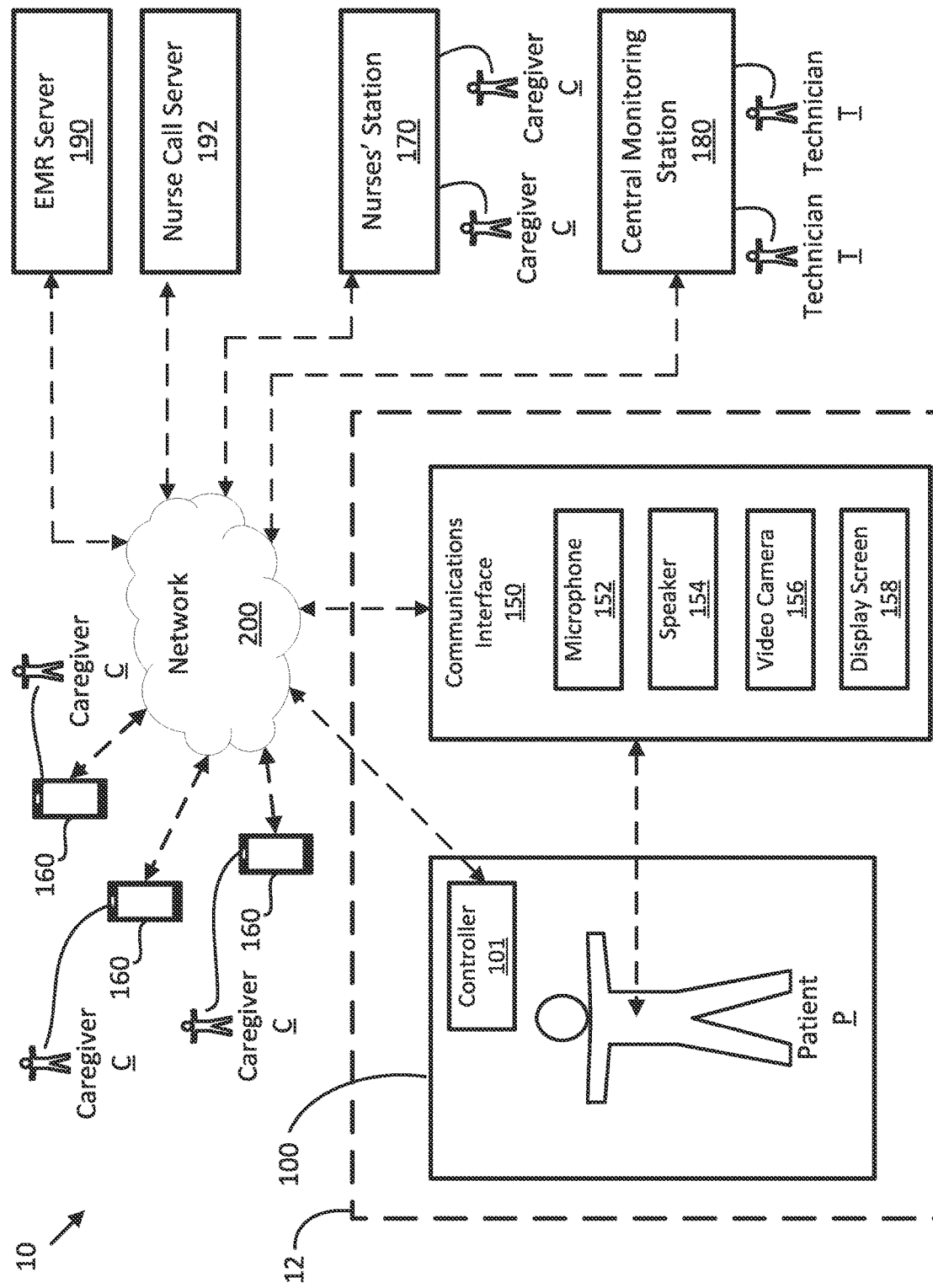
FIG. 1 schematically illustrates a system for remotely engaging and managing a patient environment.

FIG. 1 schematically illustrates a system 10 that includes a plurality of mobile devices 160 each equipped with a caregiver application 600 for remotely engaging and managing a patient environment 12. The caregiver application 600 will be described in more detail with reference to FIG. 6. In some examples, the patient environment 12 is a room where a patient P is located within a healthcare facility such as a hospital, clinic, nursing home, and the like.

In the example illustrated in FIG. 1, the patient environment 12 includes a patient support apparatus 100 on which the patient P rests. In certain examples, the patient support apparatus 100 is a hospital bed. Alternatively, the patient support apparatus 100 can be a chair, a recliner, surgical table, or any other type of support apparatus on which a patient can rest.

Each mobile device 160 is carried by a caregiver C during his or her shift. The caregiver application 600 allows the caregivers C to use his or her mobile device 160 to conduct voice, video, and text messaging between themselves, monitor alerts and calls from patients, and permit voice and video communications with patients. The mobile devices 160 are computing devices, and can include smartphones, tablet computers, or similar devices.

The patient environment 12 further includes a communications interface 150 that includes a microphone 152, a speaker 154, a video camera 156, and a display screen 158. Other examples of the communications interface 150 may include additional, different, or fewer components. For example, some examples may not include the display screen 158.

The communications interface 150 is connected to a network 200 allowing communications between the communications interface 150 and the mobile devices 160. The connection between the communications interface 150 and the mobile devices 160 via the network 200 can provide two-way audio communications between the patient P and a caregiver C, and one-way or two-way video communications between the patient P and a caregiver C.

The network 200 can include any type of wired or wireless connections or any combinations thereof. Example connections include broadband cellular networks such as 5G. In some embodiments, wireless connections can be accomplished using Wi-Fi, and the like.

The system 10 can further include a nurse call server 192 that manages the communications sent between the communications interface 150 and the mobile devices 160, as well as communications between the mobile devices 160 and a nurses' station 170 and a central monitoring station 180 that will be described in more detail below. The nurse call server 192 can enhance the communication between the patient P and the caregivers C.

Still referring to FIG. 1, the patient support apparatus 100 includes a controller 101 connected to the network 200. Accordingly, the controller 101 is connected to mobile devices 160 via the network 200. The connection between the controller 101 and the mobile devices 160 via the network 200 can provide data collected from the patient support apparatus 100 for display on the mobile devices 160. Also, a caregiver C can utilize a mobile device 160 to send signals to the controller 101 via the network 200 to control the operation of the patient support apparatus 100 when the caregiver C is remotely located away from the patient environment 12.

The nurses' station 170 is an area in a healthcare facility, such as a hospital or nursing home, where caregivers C such as nurses' and other health care staff work when not working directly with the patient P such as where they can perform administrative tasks. The nurses' station 170 includes one or more computing devices connected to the network 200.

The controller 101 is connected to the nurses' station 170 via the network 200. The computing devices in the nurses' station 170 are equipped with the caregiver application 600 (see FIG. 6) such that the connection between the controller 101 and the nurses' station 170 via the network 200 allows caregivers C located at the nurses' station 170 to conduct voice and video communications with the patient P, remotely monitor alerts and patient data from devices located in the patient environment 12, and remotely manage the patient environment 12.

The connection between the controller 101 and the nurses' station 170 via the network 200 can provide data collected from the patient support apparatus 100 for display on the one or more computing devices located in the nurses' station 170. Additionally, a caregiver C can send signals from the nurses' station 170 to the controller 101 via the network 200 to control the operation of the patient support apparatus 100 when the caregiver C is located in the nurses' station 170 such that the caregiver C is remotely located from the patient environment 12.

The central monitoring station 180 is an area outside of the patient environment 12 where technicians T monitor the patient P and can generate alerts to trigger interventions by caregivers C. The central monitoring station 180 includes one or more computing devices connected to the network 200. In some examples, central monitoring station 180 is located within the healthcare facility, but in a location remote from the patient environment 12 such as on a different floor, building, or campus of the healthcare facility. In some examples, the central monitoring station 180 is located off-site from the healthcare facility.

The controller 101 is connected to the central monitoring station 180 via the network 200. The computing devices in the central monitoring station 180 are equipped with the caregiver application 600 (see FIG. 6) such that the connection between the controller 101 and the central monitoring station 180 via the network 200 allows the technicians T to conduct voice and video communications with the patient P, remotely monitor alerts and patient data from devices located in the patient environment 12, and remotely manage the patient environment 12.

The connection between the controller 101 and the central monitoring station 180 via the network 200 can provide data collected from the patient support apparatus 100 for display on one or more computing devices located in the central monitoring station 180. A technician T can send signals to the mobile devices 160 and/or the nurses' station 170 to trigger on-site intervention by the caregivers C. In addition to sending the signals to the mobile devices 160 and nurses' station 170, the technician T can also send signals directly to the controller 101 via the network 200 to control the operation of the patient support apparatus 100.

As shown in FIG. 1, the system 10 further includes an electronic medical record (EMR) server 190. The EMR server 190 stores patient data collected from devices located in the patient environment 12, including the patient support apparatus 100, in an electronic medical record (EMR) (alternatively termed electronic health record (EHR)) of the patient P. Examples of patient data obtained from the patient support apparatus 100 can include, without limitation, patient vital signs, patient weight, and patient movement data.

Figure 2:
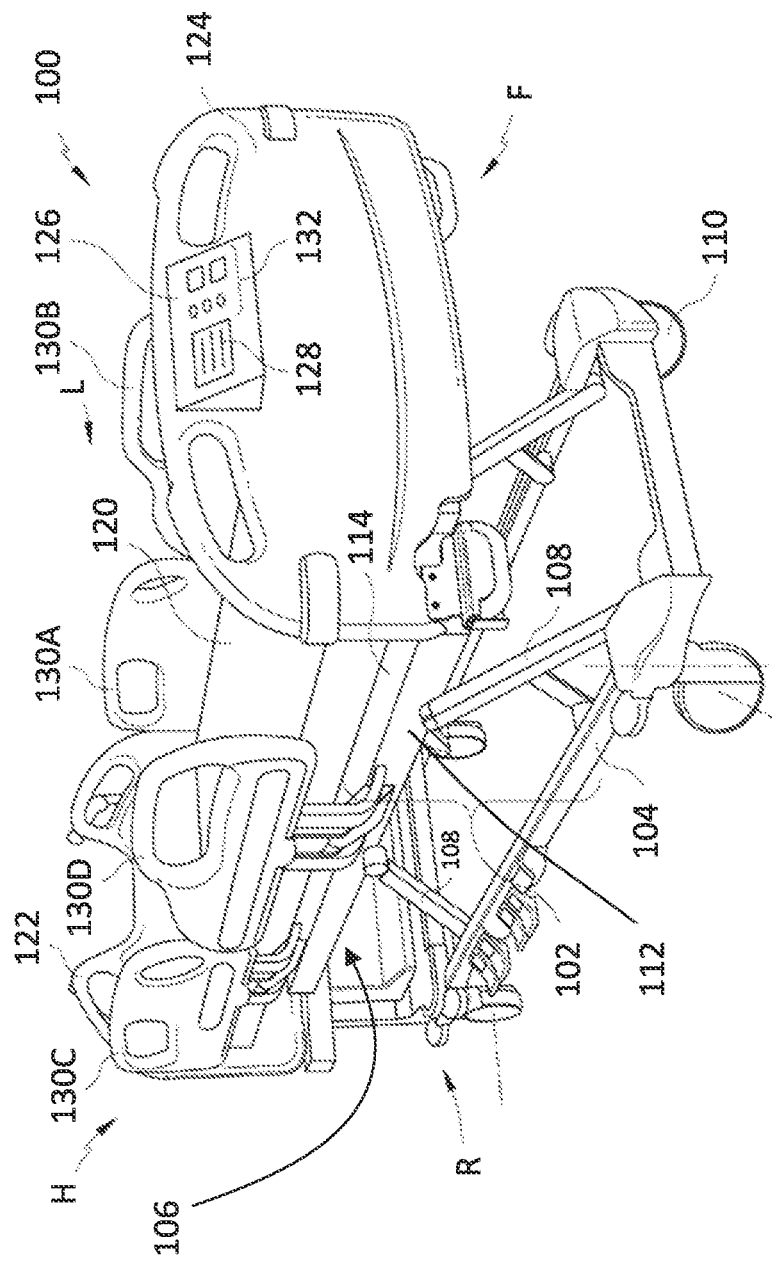
FIG. 2 illustrates an example patient support apparatus of the patient environment of FIG. 1.

FIG. 2 illustrates in more detail the patient support apparatus 100. While FIG. 2 depicts the patient support apparatus 100 as a hospital bed, alternative embodiments are possible where the patient support apparatus 100 may be a chair, a recliner, surgical table, or any other type of support apparatus. Thus, the description provided herein is not limited to hospital beds.

The patient support apparatus 100 extends longitudinally from a head end H to a foot end F and laterally from a left side L to a right side R, where left and right are taken from the perspective of a supine patient resting on the patient support apparatus 100. The patient support apparatus 100 includes a frame 102 that has a base frame 104 and an elevatable frame 106 that is supported on the base frame 104 by supports 108. The elevatable frame 106 is vertically moveable relative to the base frame 104. The frame 102 includes wheels 110 extending from the base frame 104 to the floor to facilitate the portability of the patient support apparatus 100.

The elevatable frame 106 has a sub-frame 112 and a deck 114 that supports a mattress 120. In certain embodiments, the deck 114 is segmented into an upper body section corresponding to a supine occupant's torso, a seat section corresponding to the occupant's buttocks, a thigh section corresponding to the occupant's thighs, and a calf section corresponding to the occupant's calves and feet. Alternative arrangements for the deck 114 are possible.

The mattress 120 is flexible and conforms to the profile of the deck 114 as the orientation of the various segments of the deck 114 are adjusted with respect to one another between horizontal and vertical orientations. The mattress 120 includes one or more bladders that can be inflated and deflated to adjust the firmness of the mattress.

The patient support apparatus 100 includes a left siderail assembly having at least one left siderail mounted on the left side of the frame and a right siderail assembly having at least one right siderail mounted on the right side of the frame. In example embodiment of FIG. 2, the left siderail assembly includes an upper left siderail 130A and a lower left siderail 130B, and the right siderail assembly includes an upper right siderail 130C and a lower right siderail 130D.

In certain embodiments, the upper siderails 130A, 130C are connected to an upper body section of the deck 114 and rotate with the upper body section as that section rotates, while the lower siderails 130B, 130D are connected to a portion of the elevatable frame 106 that does not rotate with respect to the sub-frame 112. Accordingly, the lower siderails 130B, 130D are always at a fixed orientation relative to sub-frame 112 as shown in FIG. 2.

Each siderail 130A-130D is positionable at a deployed position at which its upper edge is higher than the top of the mattress 120 and at a stowed position at which its upper edge is lower than the top of the mattress 120. When the deployed position, the siderail prevents the patient P from exiting the patient support apparatus 100. When in the stowed position, the siderail allows the patient P to enter and exit the patient support apparatus 100. In some embodiments, the siderails 130A-130D are also positionable at intermediate positions that are not as high as the deployed position nor as low as the stowed position. In the example embodiment illustrated in FIG. 2, all four siderails 130A-130D are in the deployed position.

The patient support apparatus 100 includes a headboard 122 and a footboard 124. In certain embodiments, the footboard 124 is removable from the foot end F of the frame 102 in order to accommodate occupant egress from the foot end F. For example, in certain embodiments, the patient support apparatus 100 can be adjusted so that its profile mimics that of a chair. When the patient support apparatus 100 is in a chair-like profile, the footboard 124 can be removed to facilitate egress and ingress at the foot end F of the patient support apparatus 100.

The patient support apparatus 100 can further include a user interface 126 for operation by a clinician. The user interface 126 includes a display 128 for displaying information, and user input devices 132 such as buttons, switches, or a keyboard. In the example embodiment illustrated in FIG. 2, the user interface 126 is positioned on the footboard 124.

Figure 3:
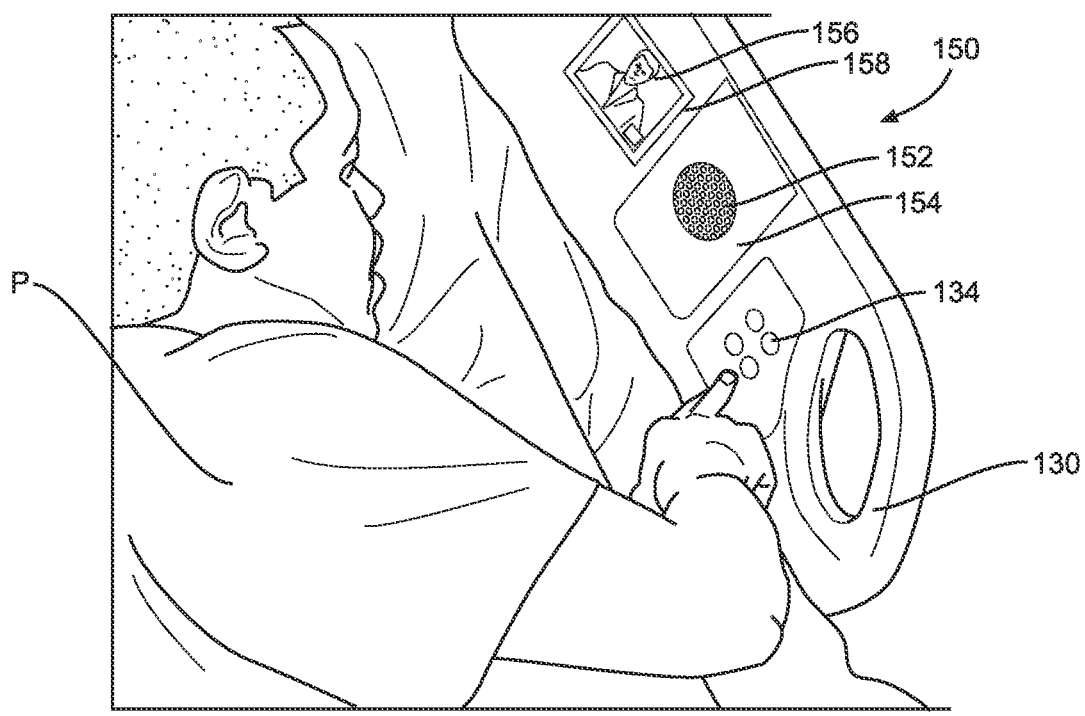
FIG. 3 illustrates an example communications interface provided on a siderail of the patient support apparatus of FIG. 2.

FIG. 3 illustrates an example of the communications interface 150 that is provided on a siderail 130 of the patient support apparatus 100. In this example, the patient P can access the microphone 152 and speaker 154 on the siderail 130 to engage in two-way audio communication with a caregiver C. Also, the video camera 156 can be provided on the siderail 130 to record a live video feed of the patient P that can be viewed by a caregiver C on a mobile device 160 or a computing device in the nurses' station 170, or that can be viewed by a technician T in the central monitoring station 180. In examples where the caregiver application provides two-way video communication, a display screen 158 can be provided on the siderail 130 so that the patient P can view a video feed of a caregiver C while the patient P communicates with the caregiver.

In some examples, the siderail 130 can further include a user input interface 134 that is operable by the patient P to adjust the position of the patient support apparatus 100. In some examples, the user input interface 134 can be used by the patient P to send a nurse call.

Figure 4:
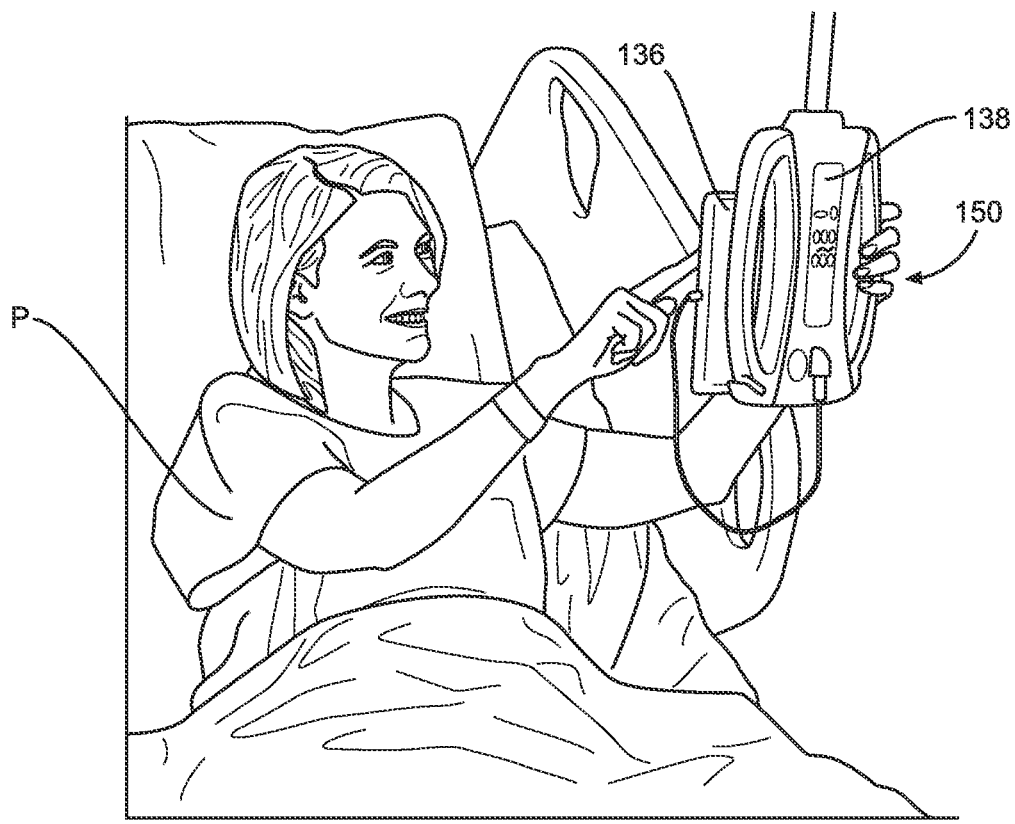
FIG. 4 illustrates another example communications interface provided on a tablet computer attached to an arm positioned over the patient support apparatus of FIG. 2.

FIG. 4 illustrates another example of the communications interface 150 that is provided on a tablet computer 136. In this example, the tablet computer 136 is attached to an arm 138 positioned over the patient support apparatus 100. The arm 138 can be raised, lowered, and swiveled to position the tablet computer 136 in a convenient location that is accessible by the patient P. In this example, the tablet computer 136 can include the microphone 152, speaker 154, video camera 156, and display screen 158 of the communications interface 150.

In some alternative examples, the tablet computer 136 is not attached to the arm 138. In such alternative examples, the tablet computer 136 can be handheld by the patient P.

Figure 5:
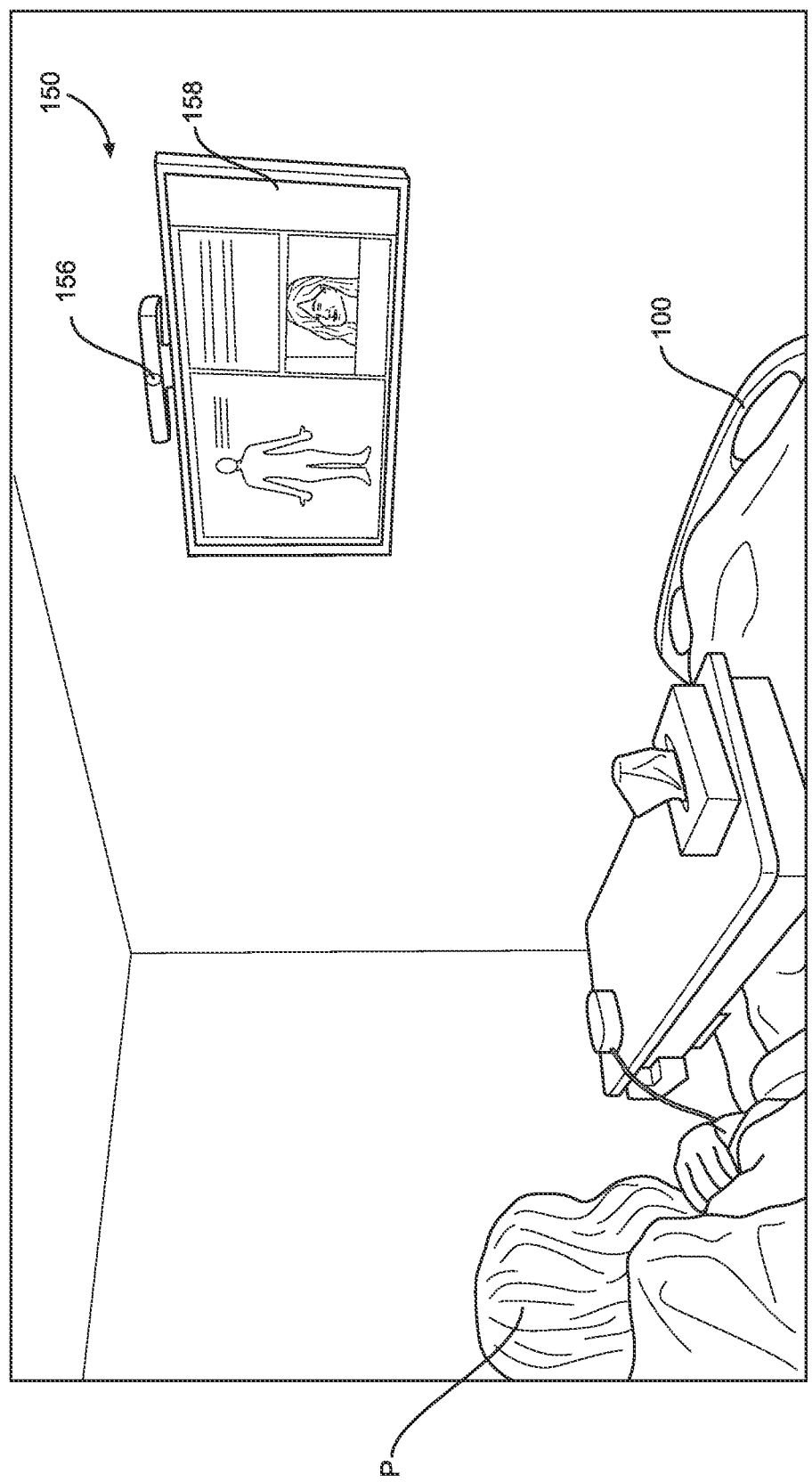
FIG. 5 illustrates another example communications interface that includes a video camera and display screen positioned in front of the patient support apparatus of FIG. 2.

FIG. 5 illustrates another example of the communications interface 150 that includes the video camera 156 and display screen 158 positioned in front of the patient support apparatus 100. In this example, the video camera 156 and display screen 158 are mounted to a wall of the patient environment 12. In alternative examples, the video camera 156 and display screen 158 can be mounted on a portable cart that can be positioned in front of the patient support apparatus 100. In this example, the video camera 156 provides a wide angle view of the patient support apparatus 100 and patient environment 12. In some examples, more than one video camera is included in the patient environment 12 such that multiple video cameras can be used to provide multiple video feeds from different angles within the patient environment 12.

In some examples, the microphone 152 and speaker 154 are provided adjacent to the display screen 158 positioned in front of the patient support apparatus 100. In alternative examples, microphone 152 and speaker 154 can be positioned on the patient support apparatus 100 such as on the siderail 130 so that the patient P can more easily hear the audio communications from the caregivers C, and can more easily talk into the microphone 152.

Figure 6:
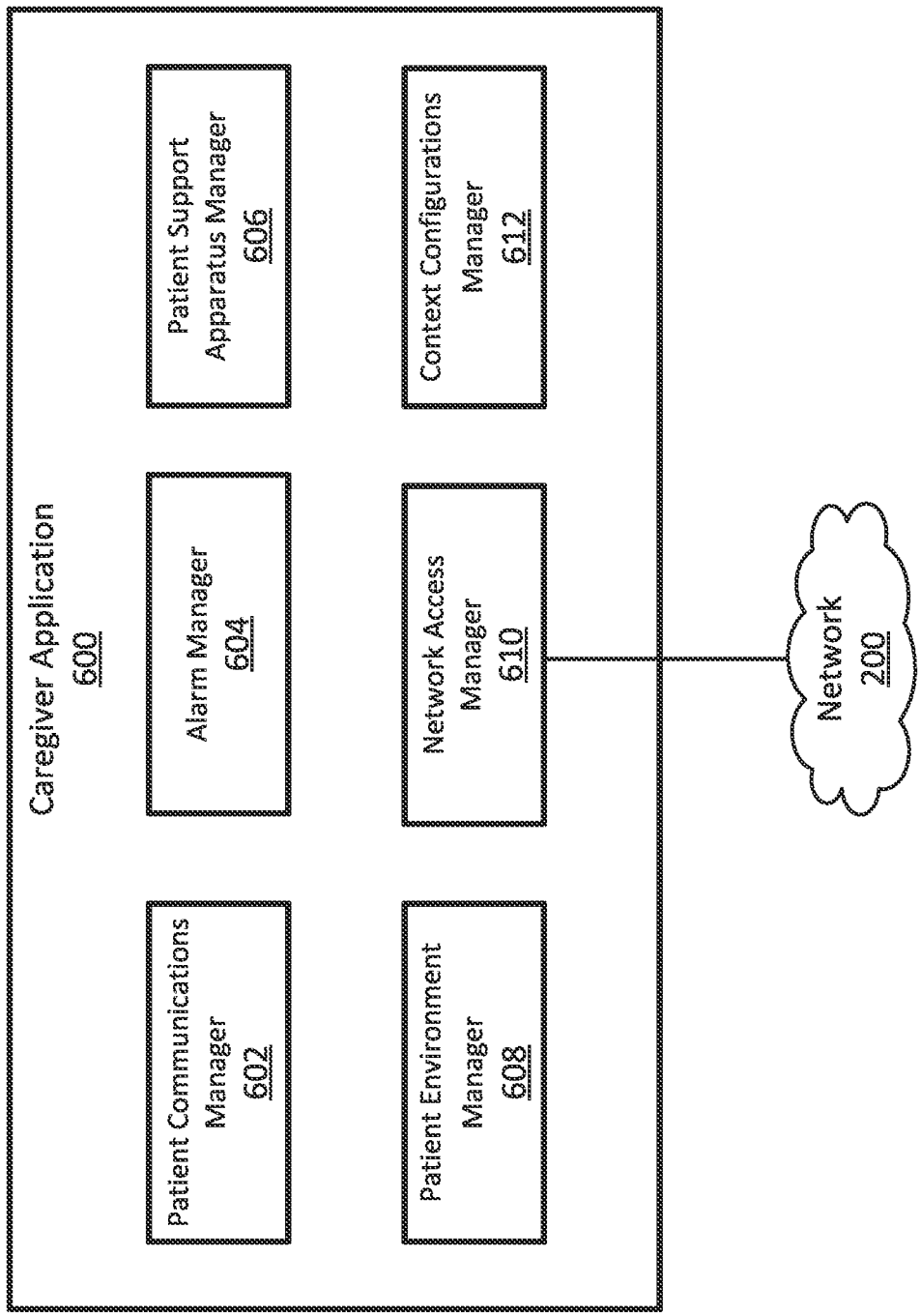
FIG. 6 schematically illustrates a caregiver application that can be implemented on one or more computing devices of the system of FIG. 1.

FIG. 6 schematically illustrates an example of the caregiver application 600. As described above, the caregiver application 600 can be operated on the mobile devices 160, on the computing devices of the nurses' station 170, and on the computing devices of the central monitoring station 180. As shown in FIG. 6, the caregiver application 600 includes a patient communications manager 602, an alarm manager 604, a patient support apparatus manager 606, a patient environment manager 608, a network access manager 610, and a context configurations manager 612. Other alternative examples of the caregiver application 600 may include additional, different, or fewer components than those shown in FIG. 6.

The network access manager 610 operates to communicate with other computing devices over one or more networks, such as the network 200. Examples of the network access manager include wired network interfaces and wireless network interfaces. Wireless network interfaces includes BLUETOOTH® wireless technology, 802.11a/b/g/n/ac, and cellular or other radio frequency interfaces in at least some possible examples.

The patient communications manager 602 manages communications between the communications interface 150 in the patient environment 12 and the mobile devices 160 and the computing devices in nurses' station 170 and central monitoring station 180. The patient communications manager 602 can manage two-way audio communications between the patient P and a caregiver C, and one-way or two-way video communications between the patient P and a caregiver C. The audio and video communications can be provided on the mobile devices 160 that are carried by the caregivers C, and on the computing devices located in the nurses' station 170. Also, the patient communications manager 602 can manage two-way audio communications between the patient P and a technician T at the central monitoring station 180, and one-way or two-way video communications between the patient P and the technician T.

Figure 7:
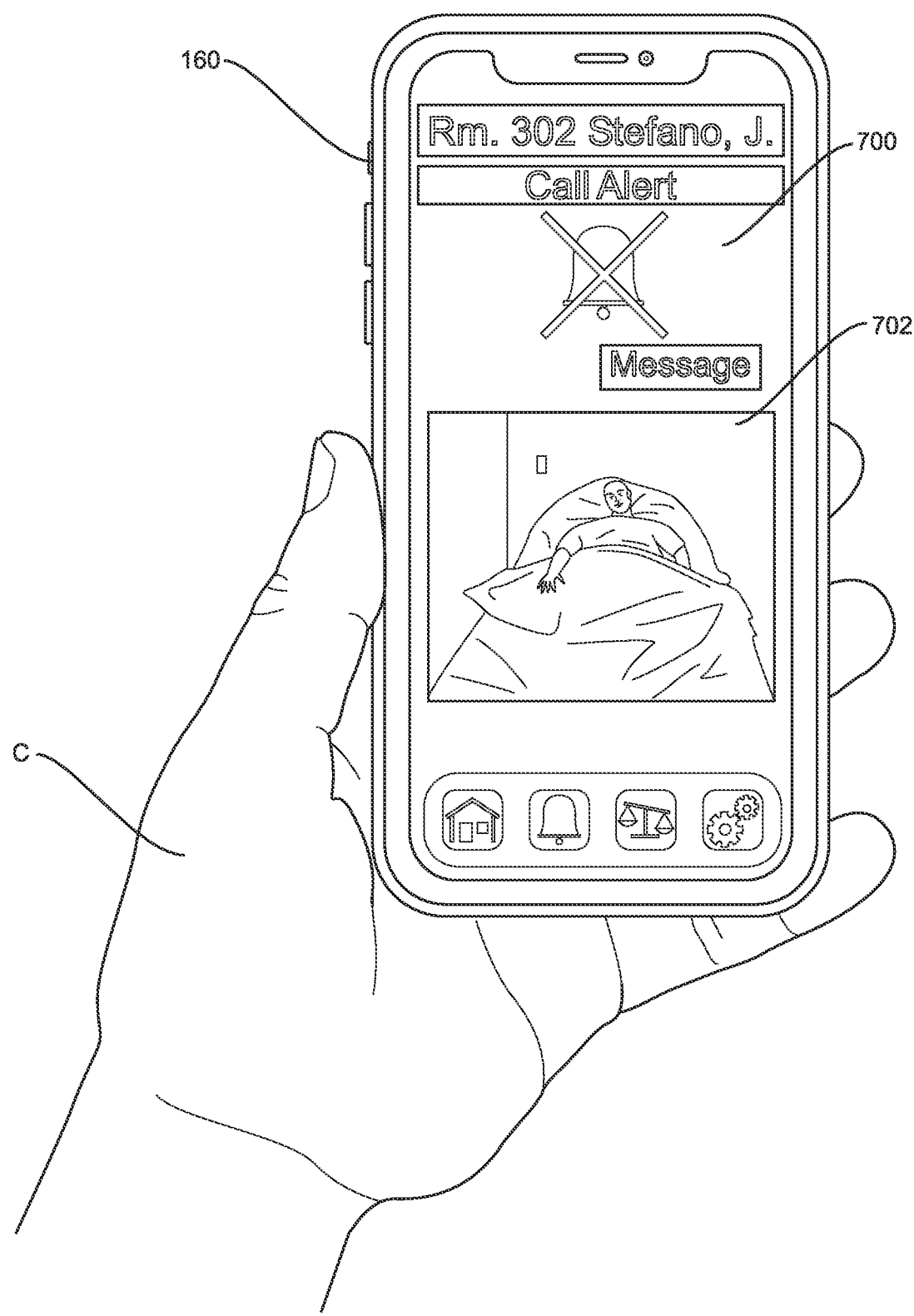
FIG. 7 illustrates an example user interface provided by the caregiver application on a mobile device used by a caregiver.

FIG. 7 illustrates an example user interface 700 provided by the caregiver application 600 on a mobile device 160 used by a caregiver C. Referring now to FIG. 7, the patient communications manager 602 can display a live video feed 702 of the patient P on the mobile device 160, and allow the caregiver C to engage in two-way audio communications with the patient P, and one-way video communications between the patient P. In some instances, the patient communications manager 602 utilizes a camera of the mobile device 160 to provide a video feed of the caregiver C on a display screen 158 in the patient environment 12 (e.g., see FIGS. 3-5) to allow the caregiver C and patient P to engage in two-way video communications.

Figure 8:
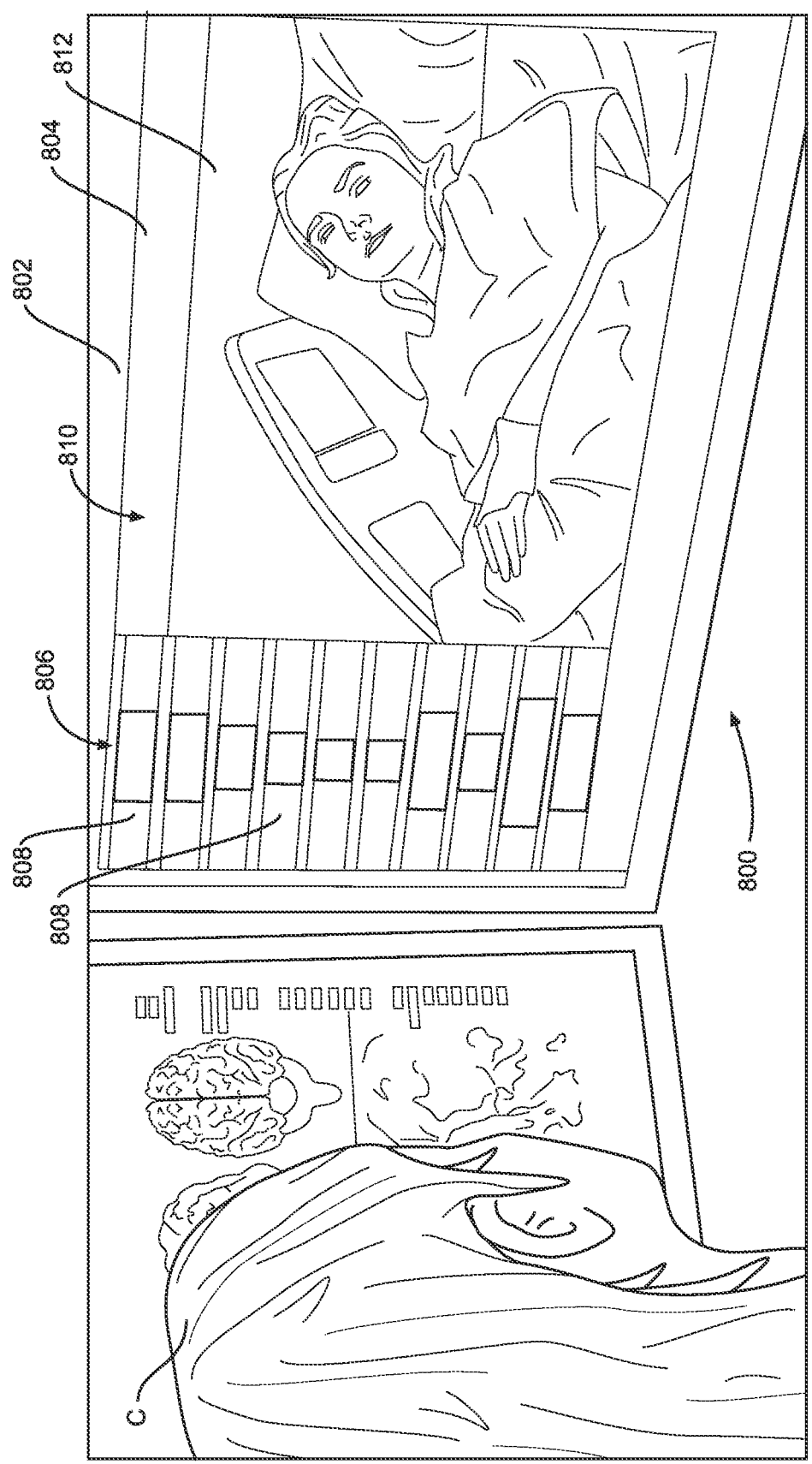
FIG. 8 illustrates an example user interface provided by the caregiver application on a computing device in a nurses' station or a central monitoring station.

FIG. 8 illustrates an example of a computing device 800 in the nurses' station 170 or the central monitoring station 180 that includes a display screen 802 that displays an example user interface 804 generated by the caregiver application 600. In example of FIG. 8, the user interface 804 includes a first pane 806 that has a plurality of video feeds 808 of patients located in the healthcare facility, and further includes a second pane 810 that is an enlarged video feed 812 of the patient P located in the patient environment 12.

The user interface 804 allows a caregiver C such as a nurse in the nurses' station 170 or a technician T in the central monitoring station 180 to engage in two-way audio communications with the patient P, and one-way video communications between the patient P. In some instances, the patient communications manager 602 utilizes a camera that is connected to or that is a part of the computing device 800 to provide a video feed of the caregiver C on a display screen 158 in the patient environment 12 (e.g., see FIGS. 3-5) to allow the caregiver C and patient P to engage in two-way video communications.

The remote vigilance of the patient P provided by the user interfaces 700, 804 can improve the speed with which patient deterioration such as seizures and mental changes are recognized. Additionally, the remote vigilance of the patient P provided by the user interfaces 700, 804 can improve protocol compliance, such as by remote implementation of a fall risk protocol, and improve alarm management response time by reducing the time needed to recognize false alarms or to escalate an alert upon confirmation of an alarm condition.

Referring back to FIG. 6, the alarm manager 604 of the caregiver application 600 can be used to remotely control one more alarms in the patient environment 12. For example, the video feeds 702, 812 in the example user interfaces 700, 900 can provide visual confirmation of an alarm condition within the patient environment 12, and a caregiver C can use the alarm manager 604 to control an alarm based on the visual confirmation such as to reset an alarm in the case of a false alarm, or escalate a response when the alarm condition is confirmed.

As an illustrative example, when an exit alarm is triggered by the patient P moving on the patient support apparatus 100 and it is a false alarm, the video feeds 702, 812 can provide a visual confirmation for a caregiver C remotely located outside of the patient environment 12 that it is a false alarm and that the patient P remains in bed. The caregiver C can then briefly communicate with the patient P using the patient communications manager 602 to confirm that the patient P is safe, and then reset or silence the exit alarm using the alarm manager 604.

As another illustrative example, when the patient P is trying to leave the patient support apparatus 100 such that the exit alarm is not a false alarm, a caregiver C remotely located outside of the patient environment 12 can briefly communicate using the patient communications manager 602 to let the patient P know that the caregiver C is on their way and for the patient P stop exiting the patient support apparatus 100 and instead wait for the caregiver C to arrive. In certain examples, the caregiver C can use remote management capabilities provided by the caregiver application 600 on the mobile device 160 to automatically optimize the patient support apparatus 100 for patient egress such as by suspending the exit alarm and siderail alarm, and adjusting the head of the bed to have a 60 degree as the caregiver C walks toward the patient support apparatus 100 and before the caregiver C arrives at the patient environment 12.

In some examples, one or more user inputs that are selectable by the caregiver C to respond to the detected exit alarm are automatically displayed on the mobile device 160 by the caregiver application 600 upon detection of the exit alarm. In some examples, access to the user inputs that are selectable to respond to the exit alarm is restricted based on the caregiver C's location, the caregiver C's credentials, and the patient P's condition. See, for example, the description provided below directed to the context configurations manager 612 of FIG. 10.

As another illustrative example, the video feeds 702, 812 can provide a visual confirmation for a technician T remotely located at the central monitoring station 180 that the patient P is attempting to exit the patient support apparatus 100 or has already exited such that the exit alarm is confirmed. When this occurs, the technician T can utilize the patient communications manager 602 to communicate to the patient P through the communications interface 150 that they should remain in the patient support apparatus 100, and wait for assistance from a caregiver C. The technician T can also send an alert to the mobile devices 160 to notify the caregivers C that the patient P is attempting to exit the patient support apparatus 100 or has already exited, and that the caregivers C should intervene to help assist the patient P.

Alternatively, the video feeds 702, 812 can show that the patient P is moving on the patient support apparatus 100 to reach for an item next to the patient support apparatus 100 such that the exit alarm is a false alarm. When this occurs, the technician T can remotely reset the exit alarm without requiring a caregiver C to physically enter the patient environment 12 to manually reset the exit alarm. In some examples, an alert is sent to the mobile devices 160 to notify the caregivers C that the exit alarm has been remotely reset or silenced such that they do not need to enter the patient environment 12 to manually reset or silence the bed exit alarm.

While the foregoing illustrative examples are described with respect to an exit alarm, additional types of alarms can be controlled by the caregiver application 600. For example, vital sign alarms such as for heart rate, respiration rate, SpO₂, and the like can be similarly managed by the alarm manager 604 of the caregiver application 600.

Advantageously, the alarm manager 604 allows caregivers C to respond to alarms more quickly and efficiently, while also reducing alarm fatigue. This can improve patient safety by providing a more rapid response to exit alarms, and thereby avoiding unassisted bed exits. This can also improve care efficiency by reducing PPE waste and avoiding unnecessary handwashing for infection control. Furthermore, this improves patient satisfaction by allowing the caregiver to address an alarm with minimal disturbance to the patient.

Figure 9:
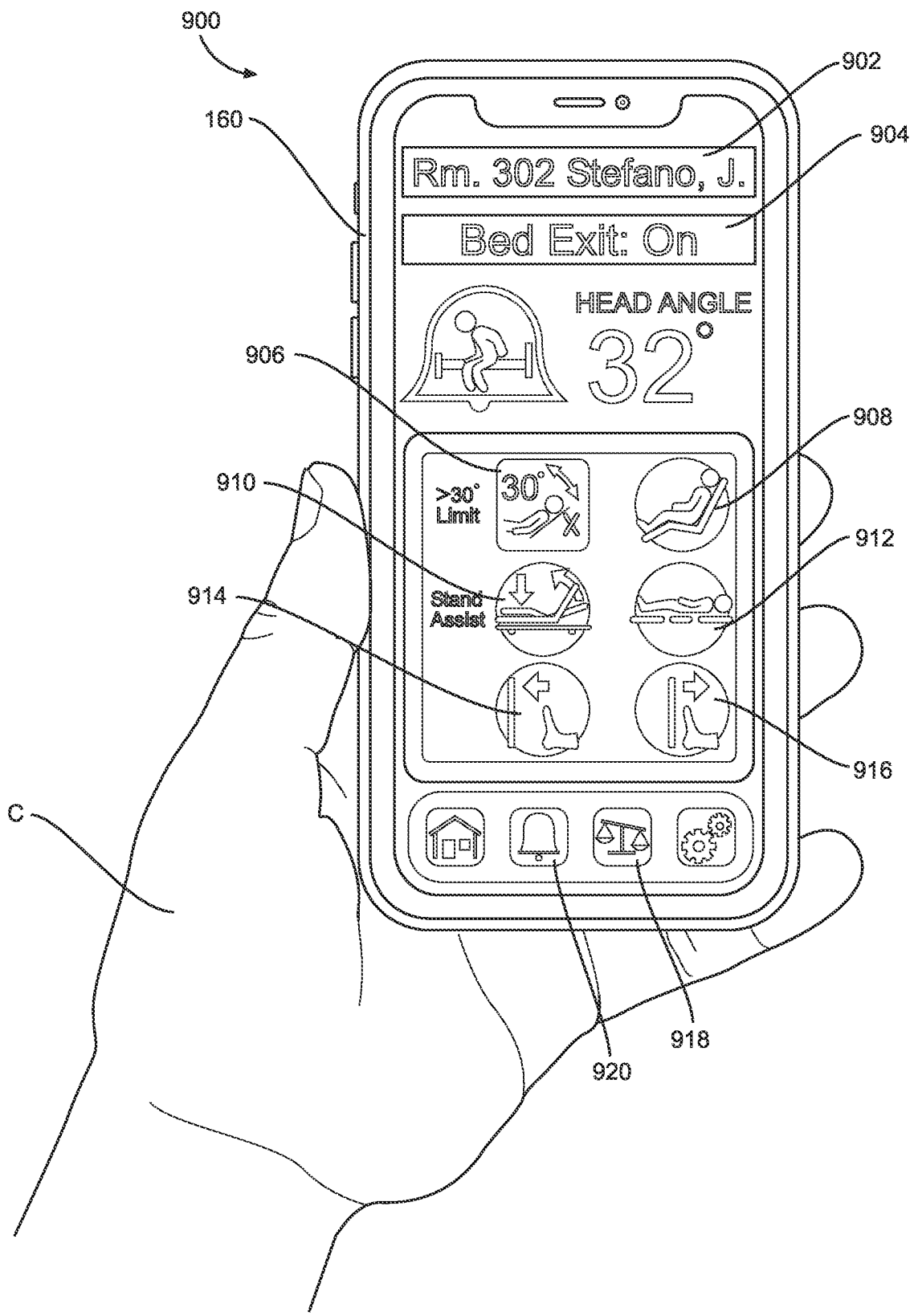
FIG. 9 illustrates another example user interface provided by the caregiver application on a mobile device used by a caregiver.

Referring back to FIG. 6, the patient support apparatus manager 606 provides remote control of the patient support apparatus 100 from outside of the patient environment 12. FIG. 9 illustrates an example user interface 900 generated by the caregiver application 600 to control the operation of the patient support apparatus 100. In the example shown in FIG. 9, the user interface 900 is displayed on a mobile device 160 used by a caregiver C. Similar user interfaces 900 for controlling the patient support apparatus 100 can be displayed on a computing device 800 (see FIG. 8) in the nurses' station 170 or central monitoring station 180.

The user interface 900 displays identification data 902 such as the name of the patient P assigned to the patient support apparatus 100, and/or the location of the patient support apparatus 100 such as a room number. The identification data 902 provides confirmation for a caregiver C that they are controlling the correct patient support apparatus.

In certain examples, the user interface 900 replicates the functions of the user interface 126 positioned on the patient support apparatus 100 (see FIG. 2) to display information obtained from the patient support apparatus 100 and provide user inputs that are selectable to control the operation of the patient support apparatus 100. For example, user interface 900 includes a user input 904 to activate, deactivate, reset, or silence an exit alarm.

The user interface 900 includes a plurality of user inputs 906-916 that are selectable to optimize the patient support apparatus 100 for patient comfort and safety. For example, a user input 906 is selectable to limit the minimum angle allowed between the upper and lower body sections of the deck 114. In certain examples, the minimum angle is 30 degrees. A user input 908 is selectable to adjust the deck 114 and mattress 120 to provide a chair-like configuration for the patient support apparatus 100. A user input 910 is selectable to adjust the lower body sections of the deck 114 to help the patient P exit the patient support apparatus 100. A user input 912 is selectable to adjust the upper and lower body sections of the deck 114 to be horizontal so that the patient P can lay flat on the patient support apparatus 100. User inputs 914, 916 are selectable to adjust the distance between the footboard 124 and the frame 102 to adjust the length of the patient support apparatus 100. The user inputs 906-916 are provided as illustrative examples and are not exhaustive. Thus, the caregiver application 600 may provide additional user inputs on the mobile devices 160 or on the computing devices in the nurses' station 170 or central monitoring station 180 that are selectable to control the patient support apparatus 100.

For example, additional user inputs provided by the caregiver application 600 on the mobile device 160 or on the computing devices in the nurses' station 170 or central monitoring station 180 to control the operation of the patient support apparatus 100 can include user inputs to adjust the deployment of the siderails 130, adjust the height of the elevatable frame 106, and to set the brakes on the wheels 110 to prevent patient support apparatus 100 from moving.

Additionally, the caregiver application 600, when installed on the mobile devices 160 or on the computing devices in the nurses' station 170 or central monitoring station 180, can display an input 918 that when selected displays the patient P's weight measured by a scale of the patient support apparatus 100, and can allow a caregiver C to remotely zero the scale.

Additional user inputs can be selected to receive and display contact free continuous monitoring (CFCM) vitals such as contactless heart rate and respiration rate measured by the patient support apparatus 100 or by a device connected thereto such as a mattress pad sensor. In some examples, the caregiver application 600 trends of the CFCM vitals over time. Additionally, the caregiver application 600 can store the CFCM vitals to the patient's EMR.

In addition to the foregoing, the caregiver application 600, when installed on the mobile devices 160 or on the computing devices in the nurses' station 170 or central monitoring station 180, allows caregivers and technicians to view trends in the patient P's movement detected by load cells in the mattress 120, and trends in the turning of the patient P such as the last time the patient P was turned, the frequency of turning the patient P, and the like.

In some examples, the functions provided by the alarm manager 604 are accessed by selecting an input 920 on user interface 900 such that additional user inputs can be displayed on the mobile device 160 or on the computing devices in the nurses' station 170 or central monitoring station 180 to activate, deactivate, reset, or silence alarms.

Also, the remote management of the patient environment 12 provided by the caregiver application 600 can improve compliance with care protocols. For example, a caregiver or technician at a remote location can view of a video feed of the patient P to visually confirm that the patient P is in compliance with personalized care protocols that have been set for the patient P such as protocols that require the upper body section of the deck 114 not to exceed 45 degrees, that require the comfort and maximum inflation modes of the mattress 120 to be disabled, and that require a therapy mode to be activated based on the patient P's condition. Such individualized care protocols can be set for the patient P to prevent falls and pressure ulcers, or to mitigate the effects of pneumonia and sleep disordered breathing. Advantageously, a remote caregiver can view the video feed of the patient P to ensure compliance with the personalized care protocols which can eliminate the need for a caregiver C to physically enter the patient environment 12 to check on the patient P, and thereby improve care efficiency.

The caregiver application 600 when installed on the mobile devices 160 or on the computing devices in the nurses' station 170 or central monitoring station 180, can provide a remote co-signature feature. In some instances, a caregiver when performing an activity in the patient environment 12 may require approval from a second caregiver. Examples may include administering "high alert" medications (e.g., Heparin drips, Insulin drips, blood product administration, etc.) that require approval from a second caregiver. The caregiver application 600 can authorize a second caregiver in a remote location (i.e., the nurses' station 170 or central monitoring station 180), and who has credentials to provide the necessary approval, to approve the activity such that it is not required to have both caregivers in the patient environment 12 at the same time. This can further improve care efficiency in the healthcare facility.

In addition to controlling the patient support apparatus 100 for patient comfort and safety, the caregiver application 600, when installed on the mobile devices 160 or on the computing devices in the nurses' station 170 or central monitoring station 180, can also provide a user input to provide remote patient turning to reduce pressure ulcers. Pressure ulcers, also called pressure injuries, decubitus ulcers, and bedsores, are injuries to skin and underlying tissue resulting from prolonged pressure on the skin that occurs due to limited movement while in bed. The user input when selected causes the bladders in the mattress 120 to inflate and deflate, and thereby move the skin and underlying tissue of the patient P. A caregiver C or technician T can observe the patient P using the video feeds 702, 812 to ensure protocol compliance and safety during the remote patient turning session, and can communicate with the patient P through the communications interface 150 to make sure that the patient P is safe and comfortable.

Figure 12:
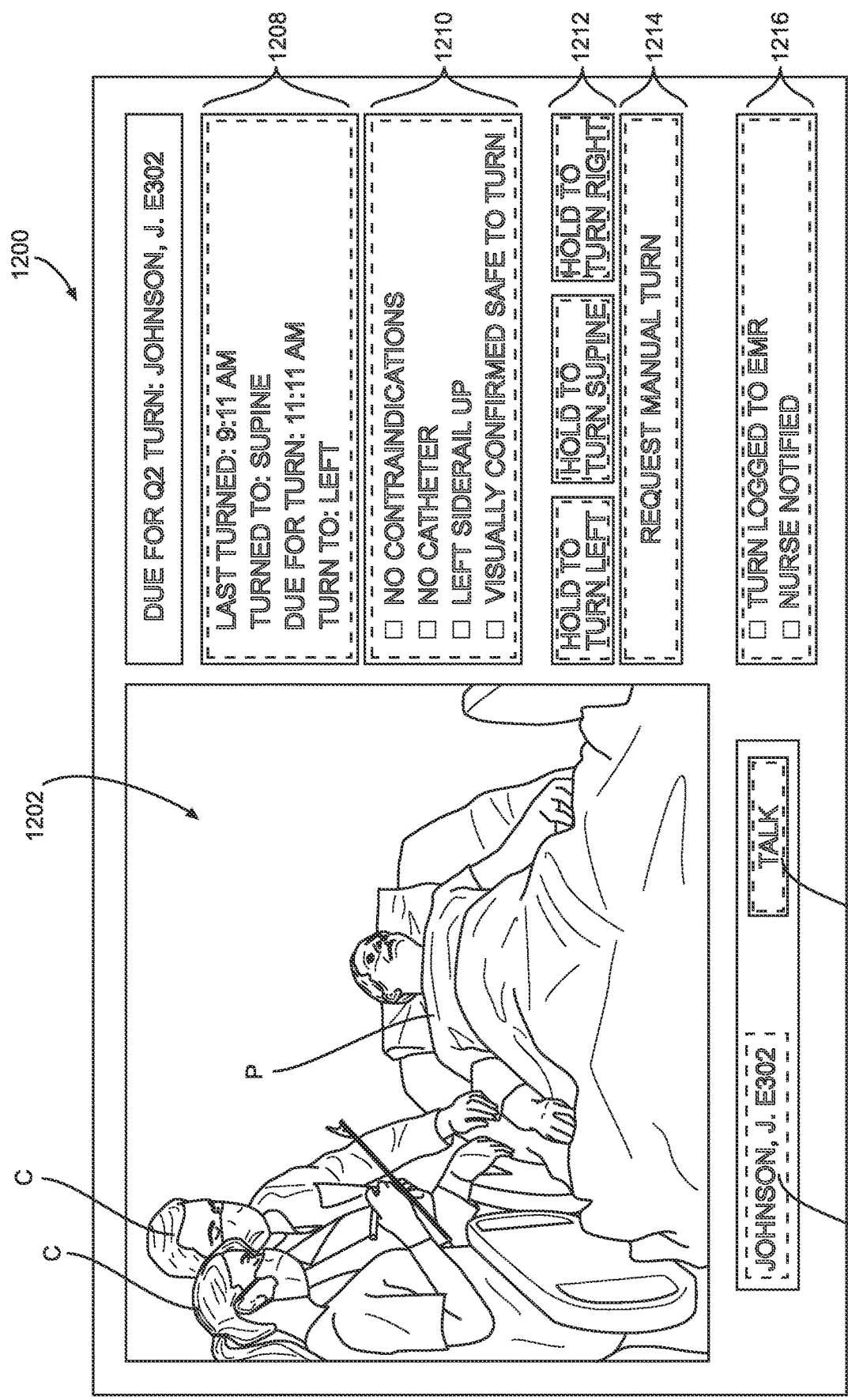
FIG. 12 illustrates an example user interface for remotely turning a patient.

FIG. 12 illustrates an example user interface 1200 for remotely turning the patient P. The user interface 1200 can be displayed by the caregiver application 600 on a mobile device 160 or on a computing device in the nurses' station 170 or central monitoring station 180. The user interface 1200 displays a video feed 1202 of the patient P during the remote patient turning, and displays data 1204 that identifies the patient P's name and room number.

The user interface 1200 also includes an input 1206 that when selected allows a remote caregiver or technician to communicate with the patient P using the communications interface 150 described above. For example, a remote caregiver or technician can communicate with the patient P through two-way audio, and one-way or two-way video communications to provide instructions for the patient P to turn their body to the left side or right side, or to reposition their body to a supine position (i.e., laying on their back).

The user interface 1200 includes a display panel 1208 that displays information related the scheduled turning for the patient P such as the last time that the patient P was turned (e.g., "9:11 am"), the position to which the patient P was last turned (e.g., "supine"), the time for next scheduled turning of the patient P (e.g., 11:11 am), and the position to which the patient P is to be turned during the next scheduled turning (e.g., "left side").

The user interface 1200 further includes a display panel 1210 that has a checklist that must be completed by the remote caregiver or technician to confirm that it is safe to turn the patient P. The checklist can help maintain compliance with safety protocols by confirming that there are no contraindications (i.e., that there are no conditions or factors that could cause harm to the patient if turned). The checklist can include items such as confirmation that the patient is not connected to a catheter, that the siderails 130 are in the deployed position, and to visually confirm that there are no obstructions that would prevent the patient P from turning.

The user interface 1200 further includes user inputs 1212 for adjusting the frame 102 and the bladders of the mattress 120 to facilitate the turning of the patient. For example, user inputs can be provided to help the patient P turn to the left side, to turn the patient P to the supine position, and to turn the patient P to the right side. Additionally, a user input 1214 can be provided to request assistance from a caregiver to manually turn the patient P. In some instances, upon selection of the user input 1214, a request is sent to a mobile device 160 of a caregiver C requesting that they enter to the patient environment 12 to help manually turn the patient P.

The user interface 1200 includes user inputs 1216 to store documentation of the turning to the patient P's EMR, and to send an alert to notify the patient P's assigned caregiver that the patient P is being turned or has been turned such that it is no longer necessary for the assigned caregiver to enter the patient environment 12 to manually turn the patient P.

In some examples, instead of turning the patient P remotely, an adjustment routine can be selected by a remote caregiver or technician using the caregiver application 600 to optimize the patient support apparatus 100 for manual patient turning upon arrival of a caregiver C to the patient environment 12. For example, the adjustment routine when selected disables the exit alarm, adjusts the elevatable frame 106 to an appropriate height (in some instances, the height is optimized for a specific caregiver C), positions the upper and lower body sections of the deck 114 to be flat and horizontal, and inflates the bladders of the mattress 120 to make turning of the patient P easier. This adjustment routine can improve care efficiency by eliminating the need for a caregiver C to manually adjust the patient support apparatus 100 before proceeding to manually turn the patient, which can reduce the amount of time that a caregiver C needs to spend inside the patient environment 12 in order to manually turn the patient P.

In some examples, the user inputs related to patient turning are restricted based on a caregiver C's distance to the patient environment 12. For example, the user input for the adjustment routine cannot be selected by the remote caregiver or technician to optimize the patient support apparatus 100 for patient turning unless another caregiver C is in close physical proximity to the patient environment 12 such that the other caregiver C is able to provide immediate assistance if needed during the adjustment routine. Also, the user input for the adjustment routine to optimize the patient support apparatus 100 for patient turning cannot be selected unless the other caregiver C has appropriate credentials for manually turning the patient P. Furthermore, the user input for performing the adjustment routine to optimize the patient support apparatus 100 for patient turning is blocked when the patient P's condition prevents the patient from being safely turned such as when the patient P is connected to a urinary catheter. These concepts will be described in more detail below with respect to FIG. 10.

As a further example, upon detecting that the caregiver C has completed the manually turning of the patient P, the caregiver application 600 can implement another adjustment routine that automatically returns the height of the elevatable frame 106, the position of the upper and lower body sections of the deck 114, and the inflation of the bladders of the mattress 120 to their previous settings, and can automatically activate or reset all alarms that were deactivated and/or silenced during the manual turning of the patient P. This additional adjustment routine can further improve care efficiency by reducing the amount of time that a caregiver C needs to spend inside the patient environment 12 in order to manually turn the patient P.

Additionally, the caregiver application 600, when installed on the mobile devices 160 or on the computing devices in the nurses' station 170 or central monitoring station 180, can provide a user input to optimize the patient support apparatus 100 for cardiopulmonary resuscitation (CPR). Such user input when selected causes the upper and lower body sections of the deck 114 to move into a flat, horizontal position, and the bladders of the mattress 120 to inflate to provide a firm surface that is optimal for performing CPR on the patient P.

As an illustrative example, a caregiver or technician at a remote location, such as the nurses' station 170 or central monitoring station 180, can detect a rapid deterioration of the patient P, and send an alert to a mobile device 160 of a caregiver C requesting immediate assistance. Thereafter, the caregiver or technician at the remote location can select the user input to optimize the patient support apparatus 100 for CPR such that the patient support apparatus 100 is optimized for CPR upon the caregiver C's arrival to the patient environment 12. This can help to provide a more rapid response to the patient P's deteriorating condition. Like the adjustment routine described above for patient turning, access to the user input for optimizing the patient support apparatus 100 for CPR can be restricted based on a caregiver C's distance to the patient environment 12, the caregiver C's credentials, and the patient P's condition.

Additional adjustment routines can be performed by the caregiver application 600 when installed on the mobile devices 160 or on the computing devices in the nurses' station 170 or central monitoring station 180 to optimize the patient support apparatus 100 for patient egress. This adjustment routine can include disabling the exit alarm, deploying the siderails 130 into the stowed position, tilting the upper body section of the deck 114 by 45 degrees, and adjusting the elevatable frame 106 to an optimal height for the patient P to exit the patient support apparatus. Like the adjustment routines described above, access to the user input for optimizing the patient support apparatus 100 for patient egress can be restricted based on a caregiver C's distance to the patient environment 12, the caregiver C's credentials, and the patient P's condition.

Referring back to FIG. 6, the patient environment manager 608 can be used to remotely control one or more conditions of the patient environment 12. For example, the patient environment manager 608 can be used to control the lighting of the patient environment 12 such as by turning on and off the lights, or diming the lights in the patient environment 12. Also, the patient environment manager 608 can be used to control the temperature of the patient environment 12 by controlling a thermostat in the patient environment 12. As another example, the patient environment manager 608 can be used to turn on and off a television inside the patient environment 12. Additional conditions of the patient environment 12 can be controlled by the patient environment manager 608 such that the foregoing examples are not exhaustive.

Advantageously, the patient support apparatus manager 606 and the patient environment manager 608 allow caregivers to use their mobile devices 160 to remotely manage the patient environment 12 from outside of the patient P's room. This can help improve patient safety, care efficiency, and patient satisfaction by ensuring protocol compliance, improving bed exit prevention, prioritizing alarm response, and increasing patient vigilance. Also, this can help to maintain infection control by reducing the frequency of exposure that caregivers such as nurses would ordinarily experience by going into the patient P's rooms to manage the patient environment 12, while also helping to conserve personal protective equipment (PPE).

Still referring to FIG. 6, the context configurations manager 612 operates to control access to the user inputs that are provided by the caregiver application 600 on the mobile devices 160 and other computing devices for selection by remove caregivers or technicians to control the patient environment 12 including the patient support apparatus 100.

Figure 10:
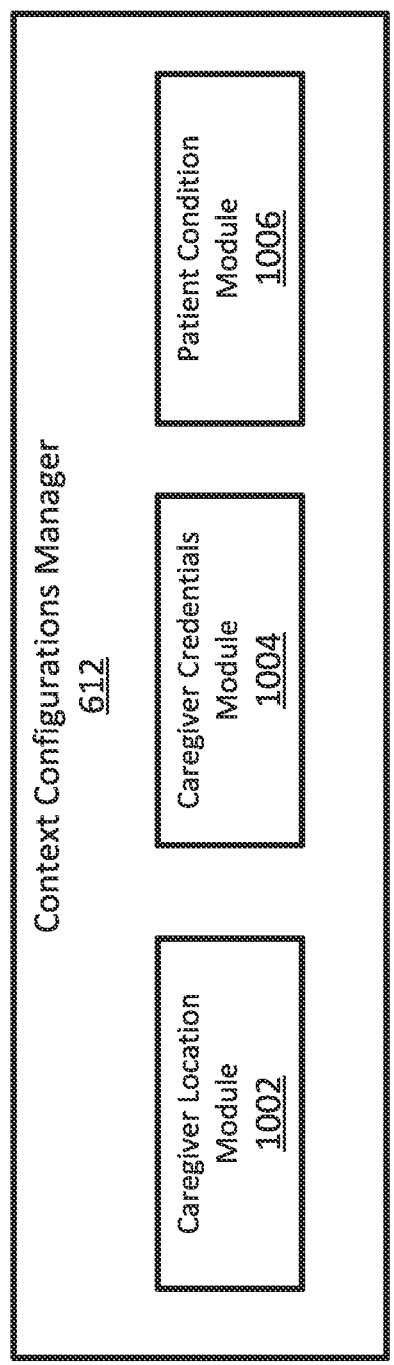
FIG. 10 illustrates an example of a context configurations manager of the caregiver application implemented on a computing device of the system of claim 1.

FIG. 10 illustrates an example of the context configurations manager 612 which includes a caregiver location module 1002, a caregiver credentials module 1004, and a patient condition module 1006. Other alternative examples of the context configurations manager 612 may include additional, different, or fewer components than those shown in FIG. 10.

The caregiver location module 1002 can limit access provided on the mobile device 160 for controlling the patient support apparatus 100, such as through the user interface 900, based on the proximity of the mobile device 160 to the patient environment 12. For example, access can be increased by activating user inputs displayed on the mobile devices 160 for controlling the patient support apparatus 100, and access can be decreased by disabling user inputs displayed on the mobile devices 160 for controlling the patient support apparatus 100.

In certain examples, each mobile device 160 includes a location-determining device that determines the location of the device relative to the patient support apparatus 100. In some embodiments, the location-determining device uses one or more of the following technologies: Global Positioning System (GPS) technology utilizing GPS signals from one or more satellites, cellular triangulation technology, network-based location identification technology, Wi-Fi positioning systems technology, real-time locating system (RTLS) technology, geofencing, near-filed communications, Bluetooth, QR code reading, and combinations thereof.

As an illustrative example, when the caregiver location module 1002 determines that a caregiver C is located beyond a predetermined distance away from the patient support apparatus 100, the user inputs provided on the mobile device 160 for controlling the patient support apparatus 100 are limited to activating an exit alarm, or resetting an exit alarm after a false alarm. When the caregiver location module 1002 determines that the caregiver C has moved closer to the patient support apparatus 100, such as a second predetermined distance that is less than the first predetermined distance, access to additional user inputs on the mobile device 160 are provided such as to disable the exit alarm. Such additional user inputs may be advantageous when the caregiver C is walking towards the patient support apparatus 100 to help the patient P exit out of the bed, such that the exit alarm is no longer required.

As a further example, when the caregiver location module 1002 determines that the caregiver C has moved closer to the patient support apparatus 100, such as a third predetermined distance that is less than the second predetermined distance, access to additional user inputs on the mobile device 160 are provided such as to adjust the positioning and orientation of the elevatable frame 106 including the profile of the deck 114, and to adjust the siderails 130 between the deployed and stowed positions. In certain examples, the third predetermined distance is within or proximate to the patient environment 12 such that the user inputs for adjusting the elevatable frame 106 and siderails 130 are not accessible on mobile device 160 unless the caregiver C is within or proximate the patient environment 12. This ensures that the caregiver C can provide immediate assistance if needed by the patient P when adjusting the position and orientation of the patient support apparatus 100 using the mobile device 160.

The caregiver location module 1002 can further detect a patient support apparatus that is closest to the mobile device 160 and automatically pair the mobile device 160 to the closest patient support apparatus without requiring input from a caregiver C. After the mobile device 160 is paired to the closest patient support apparatus, the caregiver application 600 can display on the mobile device 160 the appropriate user inputs for controlling the patient support apparatus based on the caregiver's location. Thus, when a caregiver C walks toward a certain patient support apparatus, the caregiver application 600 can automatically display the user inputs for remotely controlling that patient support apparatus, and can automatically update access to additional user inputs as the caregiver C moves closer to the patient support apparatus.

Also, the caregiver application 600 can provide a notification to the caregiver C that control on the mobile device 160 has been acquired over a patient support apparatus. For example, when the caregiver application 600 detects a patient support apparatus that is in closest proximity to the mobile device 160, a visual or auditory alert is generated to notify the caregiver C that the patient support apparatus is paired with the mobile device 160 and is ready to be controlled by the caregiver C by using the caregiver application 600.

The caregiver credentials module 1004 limits access provided on the mobile device 160 for controlling the patient support apparatus 100, such as through the user interface 900, based on the role and/or credentials of the caregiver C who is operating the mobile device 160. For example, the caregiver application 600 can require each caregiver C to login (e.g., by providing a username and password). After a caregiver C has logged-in, the caregiver application 600 can determine the role and credentials of the caregiver C based on a stored profile of the caregiver. Thereafter, the caregiver application 600 adjusts access to the user inputs for controlling the patient support apparatus 100 based on the caregiver's role and/or credentials.

The roles for various caregivers within the healthcare facility can include physician, nurse manager, registered nurse, nurse's aide, as well as non-clinical roles such as video observers and technicians located at the central monitoring station 180, housekeepers, and maintenance staff. As an illustrative example of limiting access to user inputs based on caregiver role, the caregiver credentials module 1004 can provide a registered nurse with access to user inputs for adjusting the elevatable frame 106 and siderails 130 of the patient support apparatus 100 when the registered nurse is within or adjacent the patient environment 12. In contrast, the caregiver credentials module 1004 can block a nurse's aide from having access to such user inputs even when the nurse's aide is within or adjacent the patient environment 12 because the nurse's aide does not have appropriate credentials. Instead, the caregiver credentials module 1004 limits access for the nurse's aide to only certain user inputs such as to turn on an alarm.

The caregiver credentials module 1004 allows both registered nurses and nurse's aides to view data obtained from the patient support apparatus 100 such as patient vital signs, patient weight, and patient movement data. However, in some examples, the caregiver credentials module 1004 allows the registered nurse to enter the data obtained from the patient support apparatus into the patient P's electronic medical record (EMR) stored in the EMR server 190 (see FIG. 1), and prevents the nurse's aide from entering such data into the patient P's EMR. The foregoing examples with respect to limiting access to user inputs based on caregiver role and/or credentials are not exhaustive and additional rules for restricting the level of access provided on the mobile device 160 for controlling the patient support apparatus 100 are possible.

The patient condition module 1006 limits access that is provided by the caregiver application 600 on the mobile device 160 for controlling the patient support apparatus 100 based on the condition of the patient P. For example, the patient condition module 1006 can block access to user inputs for adjusting the elevatable frame 106 of the patient support apparatus 100 when the patient P is connected to a urinary catheter such that adjusting the positioning and orientation of the deck 114 would interfere with the catheter such that it can be disconnected. As another example, when the patient P has had a hip surgery, the user inputs for turning the patient to reduce pressure injuries are blocked because turning the patient P can negatively impact the patient's recovery from the hip surgery. The foregoing examples with respect to limiting access to the user inputs on the mobile device 160 based on the patient P's condition are not exhaustive.

Figure 11:
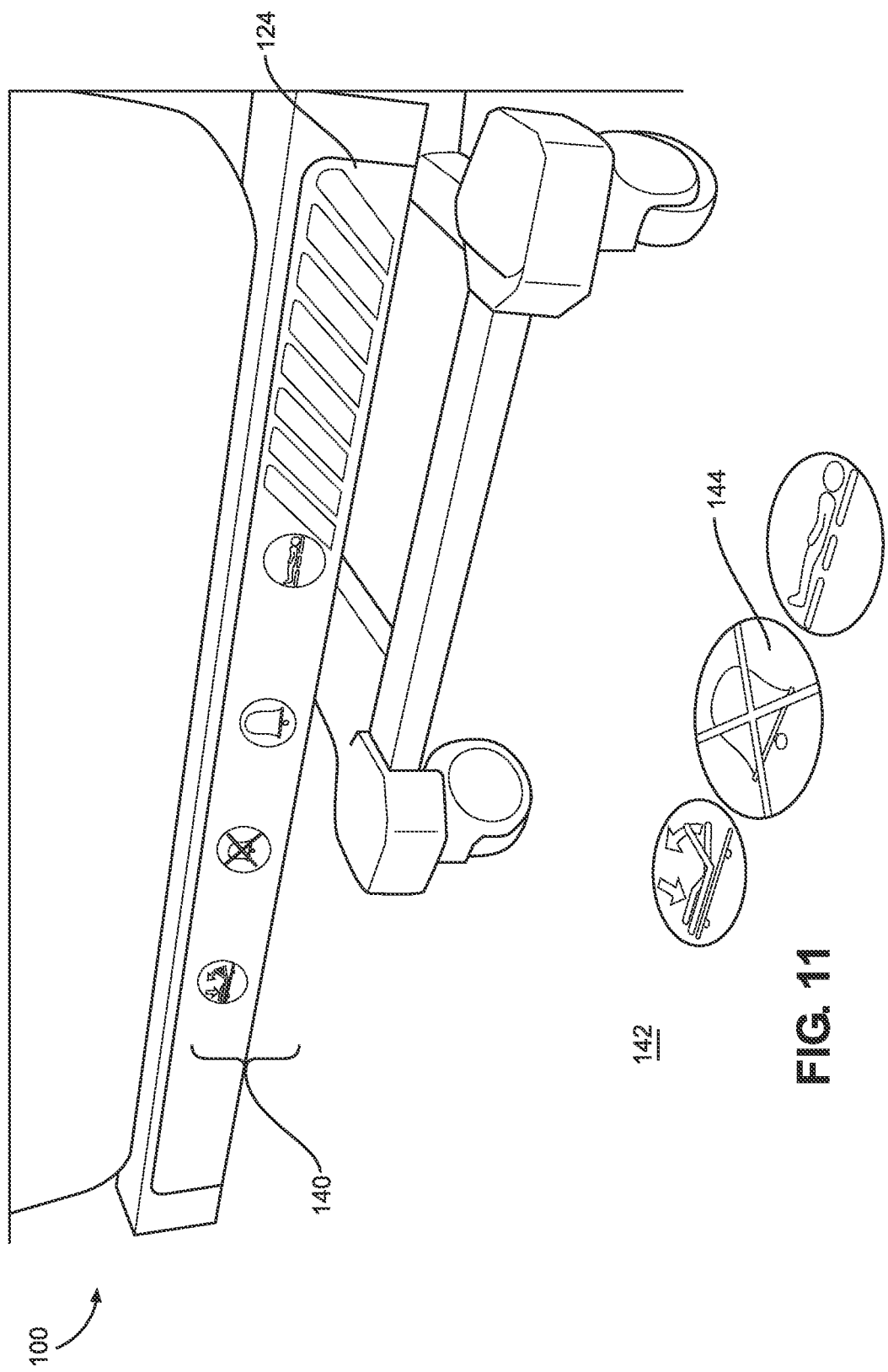
FIG. 11 shows an example of a footboard that displays a status of the patient support apparatus of FIG. 2.

FIG. 11 shows an example of a footboard 124 that displays a status 140 of the patient support apparatus 100. The status 140 is also projected by the footboard 124 onto a surface such as a floor 142 of the room where patient support apparatus 100 is located. Advantageously, the status 140 can be viewed by a caregiver from a distance such that the caregiver does not need to enter the room where the patient support apparatus is located. The caregiver can then utilize the user inputs provided by the caregiver application 600 on the mobile device 160 to control the operation of the patient support apparatus 100 without having the enter into the room.

The status 140 can indicate an unsafe condition of the patient support apparatus 100 such as an exit alarm 144 that has been disabled. The caregiver application 600 allows a caregiver to activate the exit alarm using their mobile device 160 allowing the caregiver to both recognize and address the unsafe condition from the hallway without having to enter the room. This can improve patient safety by more quickly and efficiently addressing a safety risk while also maintaining infection control. Additionally, this improves care efficiency by reducing PPE waste and avoiding unnecessary handwashing. Furthermore, this improves patient satisfaction by allowing the caregiver to address the unsafe condition without disturbing the patient.

Figure 13:
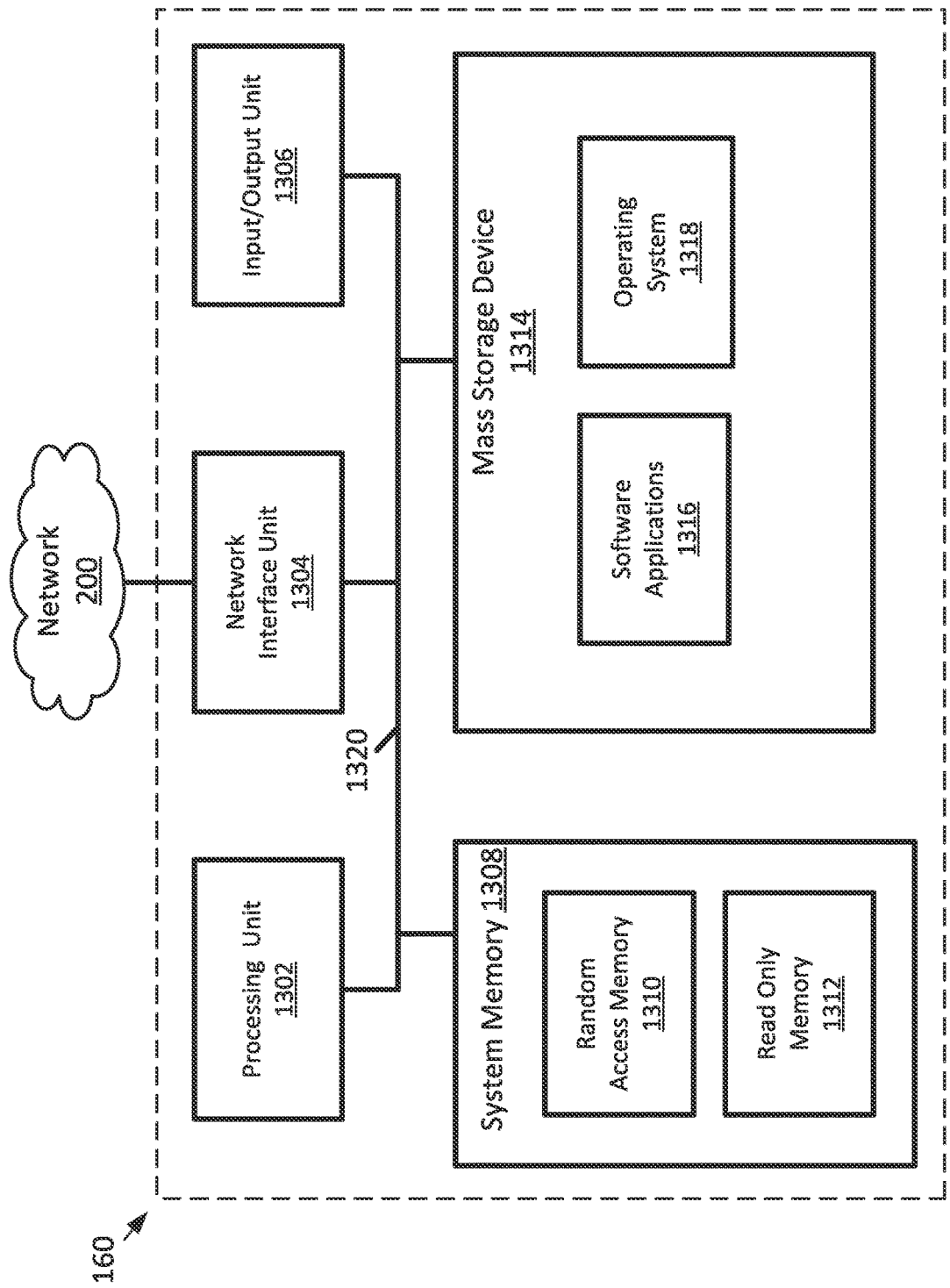
FIG. 13 schematically illustrates an example mobile device of the system of FIG. 1.

FIG. 13 schematically illustrates one of the mobile devices 160 which can be used to implement aspects of the present disclosure. Although a mobile device 160 is shown in FIG. 13, the other computing devices disclosed herein, such as the one or more computing devices located in the nurses' station 170 and the central monitoring station 180 can have similar components.

The mobile device 160 includes a processing unit 1302, a system memory 1308, and a system bus 1320 coupling the system memory 1308 to the processing unit 1302. The processing unit 1302 is an example of a processing device such as a central processing unit (CPU).

The system memory 1308 is an example of a computer readable data storage device. The system memory 1308 includes a random-access memory ("RAM") 1310 and a read-only memory ("ROM") 1312. Input/output logic containing the routines to transfer data between elements within the mobile device 160, such as during startup, is stored in the ROM 1312.

The mobile device 160 can also include a mass storage device 1314 that is able to store software instructions and data. The mass storage device 1314 is connected to the processing unit 1302 through a mass storage controller (not shown) connected to the system bus 1320. The mass storage device 1314 and its associated computer-readable data storage medium provide non-volatile, non-transitory storage for the mobile device 160.

Although the description of computer-readable data storage media contained herein refers to a mass storage device, it should be appreciated by those skilled in the art that computer-readable data storage media can be any available non-transitory, physical device or article of manufacture from which the device can read data and/or instructions. The mass storage device 1314 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The mobile device 160 may operate in a networked environment using logical connections to remote network devices, including the nurse call server 192, the nurses' station 170, the central monitoring station 180, and the EMR server 190, through the network 200, such as a local network, the Internet, or another type of network. The mobile device 160 connects to the network 200 through a network interface unit 1304 connected to the system bus 1320. The network interface unit 1304 may also be utilized to connect to other types of networks and remote computing systems.

The mobile device 160 can also include an input/output controller 1306 for receiving and processing input from a number of input devices. Similarly, the input/output controller 1306 may provide output to a number of output devices.

The mass storage device 1314 and the RAM 1310 can store software instructions and data. The software instructions can include an operating system 1318 suitable for controlling the operation of the device. The mass storage device 1314 and/or the RAM 1310 also store software instructions 1316, that when executed by the processing unit 1302, cause the device to provide the functionality of the device discussed in this document.

The various embodiments described above are provided by way of illustration only and should not be construed to be limiting in any way. Various modifications can be made to the embodiments described above without departing from the true spirit and scope of the disclosure.

What is claimed is:

1. A computing device for remotely managing a patient environment, the computing device comprising:
at least one processing device; and
at least one computer readable data storage device storing software instructions that, when executed by the at least one processing device, cause the computing device to:
display a video feed of the patient environment; and
provide user inputs that, when selected, allow a caregiver to remotely change a condition in the patient environment, wherein access to the user inputs is restricted based on at least one of a distance between the computing device and the patient environment, credentials of the caregiver, and a current condition of a patient in the patient environment, wherein:
the access to the user inputs includes a first set of user inputs when the distance between the computing device and the patient environment is less than a predetermined distance,
the access to the user inputs is restricted to a second set of user inputs when the distance between the computing device and the patient environment exceeds the predetermined distance, wherein the second set of user inputs includes at least one control for controlling an operation of a device in the patient environment, and the first set of user inputs includes the at least one control and one or more additional controls.

2. The computing device of claim 1, wherein the software instructions, when executed by the at least one processing device, further cause the computing device to:
communicate the condition in the patient environment to another caregiver.

3. The computing device of claim 1, wherein the software instructions, when executed by the at least one processing device, further cause the computing device to:
store the changed condition in the patient environment to an electronic medical record of the patient in the patient environment.

4. The computing device of claim 1, wherein the software instructions, when executed by the at least one processing device, further cause the computing device to:
provide additional user inputs that, when selected, allow the caregiver to communicate with the patient in the patient environment.

5. The computing device of claim 4, wherein communications between the patient and the caregiver include two-way audio communications between the patient and the caregiver, and one-way or two-way video communications between the patient and the caregiver.

6. The computing device of claim 1, wherein the patient environment includes a patient support apparatus having at least a frame and a mattress supported thereon, and the changed condition relates to one or more characteristics of the frame or the mattress.

7. The computing device of claim 1, wherein the user inputs are selectable to activate, deactivate, reset, or silence an alarm in the patient environment.

8. The computing device of claim 1, wherein the software instructions, when executed by the at least one processing device, further cause the computing device to:
increase access to the user inputs to remotely change the condition in the patient environment when the distance between the computing device and the patient environment decreases; and
decrease access to the user inputs to remotely change the condition in the patient environment when the distance between the computing device and the patient environment increases.

9. The computing device of claim 1, wherein the user inputs are selectable to adjust a patient support apparatus located in the patient environment to optimize the patient support apparatus for patient turning, patient egress, or cardiopulmonary resuscitation.

10. The computing device of claim 1, wherein the software instructions, when executed by the at least one processing device, further cause the computing device to:
receive contact free continuous monitoring vitals of the patient located in the patient environment from a device located in the patient environment;
trend the contact free continuous monitoring vitals over time; and
store the contact free continuous monitoring vitals to an electronic medical record.

11. The computing device of claim 1, wherein the software instructions, when executed by the at least one processing device, further cause the computing device to:
authorize the caregiver to provide remote approval of an activity being performed by another caregiver in the patient environment.

12. The computing device of claim 1, wherein the software instructions, when executed by the at least one processing device, further cause the computing device to:
receive a weight of the patient measured by a patient support apparatus located in the patient environment, and to zero a scale of the patient support apparatus.

13. A non-transitory computer-readable data storage medium comprising software instructions that, when executed, cause at least one computing device to:
display a video feed of a patient environment;
provide a user input that, when selected, allows a caregiver to communicate with a patient in the patient environment, the caregiver being remotely located away from the patient; and
provide one or more user inputs that, when selected, allow the caregiver to remotely manage the patient environment, wherein access to the one or more user inputs is restricted based on at least one of a distance between the at least one computing device and the patient environment, credentials of the caregiver, and a condition of the patient, wherein the access to the one or more user inputs includes a first set of user inputs when the distance between the computing device and the patient environment is less than a predetermined distance, the access to the one or more user inputs is restricted to a second set of user inputs when the distance between the computing device and the patient environment exceeds the predetermined distance, wherein the second set of user inputs includes at least one control for controlling an operation of a device in the patient environment, and the first set of user inputs includes the at least one control and one or more additional controls.

14. The non-transitory computer-readable data storage medium of claim 13, wherein the software instructions further cause the at least one computing device to:
increase access to the one or more user inputs to remotely manage the patient environment when the distance between the computing device and the patient environment decreases; and
decrease access to the one or more user inputs to remotely manage the patient environment when the distance between the computing device and the patient environment increases.

15. The non-transitory computer-readable data storage medium of claim 13, wherein the one or more user inputs are selectable to activate, deactivate, reset, or silence an alarm in the patient environment.

16. The non-transitory computer-readable data storage medium of claim 13, wherein the one or more user inputs are selectable to adjust a patient support apparatus located in the patient environment to optimize the patient support apparatus for patient turning, patient egress, or cardiopulmonary resuscitation.

17. A method of remotely managing a patient environment, the method comprising:
displaying a video feed of the patient environment;
providing a user input allowing a caregiver to communicate with a patient in the patient environment, the caregiver being remotely located away from the patient; and
providing one or more user inputs that, when selected, allow the caregiver to remotely manage the patient environment, wherein access to the one or more additional user inputs is restricted based on at least one of a distance between a computing device and the patient environment, credentials of the caregiver, and a condition of the patient, wherein the access to the one or more user inputs includes a first set of user inputs when the distance between the computing device and the patient environment is less than a predetermined distance, the access to the one or more user inputs is restricted to a second set of user inputs when the distance between the computing device and the patient environment exceeds the predetermined distance, wherein the second set of user inputs includes at least one control for controlling an operation of a device in the patient environment, and the first set of user inputs includes the at least one control and one or more additional controls.

18. The computing device of claim 1, wherein the at least one control is selectable to activate, deactivate, reset, or silence an alarm in the patient environment.

19. The computing device of claim 18, wherein the one or more additional controls are selectable to adjust a patient support apparatus located in the patient environment.

20. The computing device of claim 19, wherein the one or more additional controls are selectable to adjust the patient support apparatus for patient turning, patient egress, or cardiopulmonary resuscitation.

* * * * *